US008263418B2

(12) United States Patent
Brennan et al.

(10) Patent No.: US 8,263,418 B2
(45) Date of Patent: Sep. 11, 2012

(54) SENSORS FOR DETECTING AN ANALYTE USING SILVER NANOPARTICLES

(75) Inventors: Margaret Elizabeth Brennan, Templemore (IE); Gordon James Armstrong, Lower Meelick (IE); John Kelly, County Dublin (IE); Aine Marie Whelan, County Dublin (IE)

(73) Assignee: The Provost, Fellows and Scholars of the College of the Holy and Undivided Trinity of Queen Elizabeth, Near Dublin, Dublin (IE)

( * ) Notice: Subject to any disclaimer, the term of this patent is extended or adjusted under 35 U.S.C. 154(b) by 726 days.

(21) Appl. No.: 11/235,053

(22) Filed: Sep. 27, 2005

(65) Prior Publication Data

US 2006/0286684 A1 Dec. 21, 2006

Related U.S. Application Data

(63) Continuation of application No. PCT/IE2004/000047, filed on Mar. 29, 2004.

(60) Provisional application No. 60/483,010, filed on Jun. 27, 2003.

(30) Foreign Application Priority Data

Mar. 28, 2003 (IE) .................................... 2003/0234

(51) Int. Cl.
*G01N 33/553* (2006.01)
(52) U.S. Cl. ........ 436/525; 977/773; 436/518; 436/524; 435/7.1; 435/283.1; 435/287.1; 435/287.2; 435/288.7
(58) Field of Classification Search .................. 436/518, 436/524, 525; 435/7.1, 283.1, 287.1, 287.2, 435/288.1, 288.7; 422/50, 68.1, 82.05, 82.09; 977/773
See application file for complete search history.

(56) References Cited

U.S. PATENT DOCUMENTS

| 7,057,732 | B2 * | 6/2006 | Jorgenson et al. | ............ 356/445 |
| 7,122,384 | B2 * | 10/2006 | Prober et al. | .................. 436/524 |
| 7,129,096 | B2 * | 10/2006 | Chilkoti et al. | ................. 436/518 |
| 7,221,457 | B2 * | 5/2007 | Jorgenson et al. | ............ 356/445 |
| 7,225,082 | B1 * | 5/2007 | Natan et al. | ....................... 702/27 |
| 2003/0170687 | A1 * | 9/2003 | Chilkoti et al. | ................... 435/6 |
| 2004/0023415 | A1 * | 2/2004 | Sokolov et al. | ............... 436/518 |

FOREIGN PATENT DOCUMENTS

| EP | 1321761 A1 | 6/2003 |
| WO | 00/10010 | 2/2000 |
| WO | 01/25758 | 4/2001 |
| WO | WO01/51665 | 7/2001 |
| WO | WO02/087749 | 11/2002 |

OTHER PUBLICATIONS

Englebienne, Use of colloidal gold surface plasmon resonance peak shift to infer affinity constants from the interactions between protein antigens and antibodies specific for single or multiple epitopes, 1998, Analyst, vol. 123, pp. 1599-1603.*
Chen et al, J. Phys. Chem., vol. 106, No. 42, Oct. 24, 2002, pp. 10777-10781, Silver Nanodisks: Synthesis, Characterization . . . .
Oldenburg et al, Analytical Biochemistry 309, 2002, pp. 109-116 Base pair mismatch recognition using plasmon resonant . . . .
Choi et al, Radiation Physics & Chemistry 67, 2003, pp. 517-521 Interaction between the surface of the silver nanoparticles . . . .
Haes et al. J. Am. Chem. Soc. 124, 2002, pp. 10596-10604, A Nanoscale Optical Biosensor: Sensitivity & Selectivity of an . . . .
Frederix et al, Anal. Chem. 75, 2003, pp. 6894-6900, Biosensinq Based on Light Absorption of Nanoscaled Gold and Silver Particle.
Park et al, Science, vol. 295, Feb. 22, 2002, pp. 1503-1506, Array-Based Electrical Detection of DNA with Nanoparticle Probes.
Taton et al, J. Am. Chem. Soc. 123, 2001, pp. 5164-5165, Two-Color Labeling of Oligonucleotide Arrays via Size-Selective . . . .
Link et al, J. Phys. Chem. B 103, 1999, pp. 8410-8426, Spectral Properties and Relaxation Dynamics of Surface Plasmon . . . .
Mock et al, Jour. of Chem. Phys., vol. 116, No. 15, Apr. 15, 2002, pp. 6755-6759, Shape effects in plasmon resonance of individual . . . .
Jin et al, Science, vol. 204, Nov. 30, 2001, pp. 1901-1903, Photo-induced Conversion of Silver Nanospheres to Nanoprisms.
Chen et al, Nano Ltrs, vol. 2, No. 9, 2002, pp. 1003-1007, Synthesis and Characterization of Truncated Triangular Silver . . . .
Zhou et al, Advanced Mateirals, vol. 10, 1999, pp. 850-852, A Novel Ultraviolet Irradiation Photoreduction Technique for . . . .
Jana et al, Chem. Commun., 2001, pp. 617-618, Wet chemical synthesis of silver nanorods and nanowires of controllable . . . .
Haynes et al, J. Phys. Chem. B, 105, 2001, pp. 5599-5611, Nanosphere lithography: A Versatile Nanofabrication Tool for . . . .
Jensen et al, J. Phys. Chem. B, 104, 2000, pp. 10549-10556, Nanosphere Lithography: Tunable Localized Surface Plasmon . . . .
Malinsky et al, J. Am. Chem. Soc., 123, pp. 1471-1482, Chain Length Dependence and Sensing Capabilities of the Localized . . . .
Riboh et al, J. Phys. Chem. B, 107, 2003, pp. 1772-1780, A Nanoscale Optical Biosensor: Real-Time Immunoassay in . . . .
Sun et al, Nano Letters, vol. 3, No. 5, 2003, pp. 675-679, Transformation of Silver Nanospheres into Nanobelts and Triangular . . . .
Bonnemann et al, Eur. J. Inorg. Chem., 2001, pp. 2455-2480, Nanoscopic Metal Particles—Synthetic Methods and Potential . . . .
Trindade et al, Chem. Mater. 13, 2001, pp. 3843-3858, Nano-crystalline Semiconductors: Synthesis, Properties and . . . .
Shipway et al, Chem. Commun., 2001, pp. 2035-2045, Nanoparticle as structural and functional units in surface-confined . . . .
Kottmann et al, New Jour. of Physics 2, 2000, pp. 27.1-27.9, Field polarization and polarization charge distributions in . . . .
Reynolds, III et al, J. Am. Chem. Soc. 122, 2000, pp. 3795-3796 Homogeneous, Nanoparticle-Based Quantitative Colorimetric . . . .
Voisin et al., "Ultrafast Electron Dynamics and Optical Nonlinearities in Metal Nanoparticles" *J. Phys. Chem. B.* 2001, 105, 2264-2280.
Kreibig et al., "Optical Properties of Metal Clusters" *Springer Series in Materials Science* 1995, 34-37, 296-297 and 356-357.
Isabel Pastoriza-Santos et al., "Synthesis of Silver Nanoprisms in DMF," Nano Letters vol. 2, No. 8, pp. 903-905 (2002.

* cited by examiner

*Primary Examiner* — Melanie J Yu
(74) *Attorney, Agent, or Firm* — Jacobson Holman PLLC

(57) ABSTRACT

A sensor comprises silver nanoparticles in which substantially all of the surfaces of the silver nanoparticles are available for interaction with an analyte or for functionalization with a receptor which is capable of interacting with an analyte. Silver nanoparticles are prepared by forming the nanoparticles in the presence of a polymeric stabilizer such as PVA.

46 Claims, 39 Drawing Sheets

(i)

(ii)

Key to drawing:

Silver nanoparticle

Receptor (e.g.: biotin, anti-domoic acid, IgG)

Target analyte
e.g.: streptavidin, domoic acid, anti-IgG

Legend

Sensor Preparation

Sensor Function

Key to drawing:

Sensor

Target analyte
e.g.: streptavidin, Domic Acid, anti-IgG

Permeable solid surface e.g. Nitrocellulose membrane

Instructions
1. Add 1 drop of sample to test area
2. Wait for 1 minute
3. Peel off top layer
4. Compare colour of test area to colours on card.
5. Read result from panel corresponding to test area colour (iii) or Read graduated colour panel and read off corresponding detected concentration level (iv)

SENSORS FOR DETECTING AN ANALYTE USING SILVER NANOPARTICLES

This is a continuation of PCT/IE2004/000047 filed 29 Mar. 2004 and published in English, claiming the benefit of U.S. provisional application No. 60/483,010, filed 27 Jun. 2003.

The development of sensors is an area of great interest. A biological, chemical or biochemical sensor is a device capable of quantitative or qualitative recognition of a target species of interest for example peptides, metabolites, molecules or ions In the area of bio-detection there are many diagnostic methods used to detect disease pathogens, hormones, antibodies, and such like, in body fluids. Common clinical diagnostic methods include, for example, the enzyme-linked immunosorbent assay (ELISA), Western blotting, lateral flow test (LFT). In the area of chemical and environmental detection, there are many diagnostic methods used for detection, for example, titration, oxygen demand tests, chromatography, atomic absorption, spectroscopy/colorimetry. These are well-established techniques, however a multi-step process is typically required and in many cases it takes a number of hours and/or days to determine a result.

In the last few years metal nanoparticles have been found to be good candidates for use as sensing indicators.

When an external electro-magnetic field such as light is applied to a metal, the conduction electrons move collectively so as to screen the perturbed charge distribution, in what is known as "plasma oscillation". The surface plasmon resonance (SPR) is hence a collective excitation mode of the plasma localized near the metal surface.

In the case of a metal nanoparticle, the surface plasmon mode is 'restricted' due to the small dimensions to which the electrons are confined, i.e. the surface plasmon mode must conform to the boundaries of the dimensions of the nanoparticle. Therefore, the resonance frequency of the surface plasmon oscillation of the metal nanoparticle is different from the plasma frequency of the bulk metal. Surface interactions can alter the optical properties and influence the spectral profile of the light scattered by the SPR of the metal nanoparticles. This feature can be applied as an indicator in sensing interactions. Among the metal nanoparticles known to exhibit SPR, silver nanoparticles have an especially strong SPR and are expected to provide particularly high sensitivity for biosensing purposes.

Gold is the primary metal nanoparticle currently being researched for the development of bio-sensors. Since the late 1990s, a major area of research has been the development of DNA-based methods using gold nanoparticles [1-4]. In typical biosensors based on gold nanoparticles, the colour change which may be observed in the presence of a target analyte is caused primarily by aggregation rather than a change in SPR. The individual gold nanoparticles may be functionalised such that the analyte causes them to aggregate, giving rise to a colour change; whereas discrete gold nanoparticles appear crimson in colour to the naked eye, larger aggregates of gold nanoparticles appear blue.

The invention also relates to a method for the preparation of silver nanoparticles with controlled optical properties. Significantly this method uses a simple 'wet chemistry' technique for the easy production of large quantities of silver nanoparticles in a range of colours.

The optical properties of nanoparticles, such as colour or luminescence, have been found to be highly dependent on the size and shape of the nanoparticle. [5-8] Furthermore, metal nanoparticles are known to behave as catalysts. A catalyst may be defined as an agent that increases the rate at which a chemical reaction occurs. In large metallic crystals, different surfaces have different catalytic properties. Nanoparticles of different shapes also have different crystal surfaces, each of which may be expected to exhibit specific catalytic properties. Compared to macroscopic crystals, enhanced catalytic efficiency is anticipated from such shaped nanoparticles.

While considerable progress has been made in the development of synthetic methods that afford control of nanoparticle size, control of nanoparticle morphology has proved more difficult to achieve. Only a few methods for the preparation of silver nanoparticles having defined shapes have been reported. However, many of these methods have limitations which would impede their application to the bulk production of silver nanoparticles.

A technique reported by Zhou et al uses ultraviolet irradiation and poly(vinyl alcohol) (PVA) as a stabilizer to synthesize silver nanorods of length up to 350 nm (9). Such photo induced methods are expensive, often requiring long irradiation times of up to 70 hours.

Murphy et al (10) described a seeding method to obtain silver nanorods of controllable aspect ratio and lengths ranging from 40 nm to 200 nm. Cetyltrimethyl ammonium bromide (CTAB) was used to template the growth of the nanorods. The silver nanorods showed two plasmon bands in the UV-Vis absorption spectrum—one at 400 nm and another at wavelengths ranging from 900 to 1100 nm depending on the length of the nanorods. The widely used CTAB is not efficient as a stabilising agent as it is only water soluble at elevated temperatures. This poses problems for the long term stability and storage of nanomaterials produced according to this method.

Mirkin et al (7) developed a photo-induced method to prepare silver nanoprisms of edge length 100 nm by irradiation of spherical silver nanoparticles. These nanoprisms showed three plasmon resonances—at 335, 470 and 670 nm. However, this method requires irradiation conditions involving light of a specific wavelength range and requiring irradiation times of up to 125 hours.

Chen et al (8) obtained truncated triangular silver nanoplates of average edge length 68 nm through a seed mediated growth in the presence of micelles of CTAB. Again the use of CTAB provides problems for scaled up nanoparticle synthesis.

Van Duyne et al (11) reported the use of nanosphere lithography (NSL) to prepare triangular silver arrays on a solid substrate. The nanoparticles obtained via this method have a width ranging from 90 to 150 nm and have been used to develop optical bio-sensors [12-15]. NSL uses a sacrificial layer of polymer nanospheres combined with chemical vapour deposition (CVD) to produce an array of nanoparticles on a substrate. However, NSL is a complex and costly technique, and is as yet only a laboratory procedure which is not industrially proven. The primary disadvantage of this method in its application to bio-sensing is that the available sensing surface area of the silver nanoparticles is reduced due to the inactivity of the surface area bound to a solid substrate. In addition, being bound to a substrate greatly reduces the flexibility of these nanoparticles for use in bio-sensing applications.

The present invention is directed towards a detection method which overcomes many of these problems.

STATEMENTS OF INVENTION

According to the invention there is provided a sensor comprising silver nanoparticles in which substantially all of the surfaces of the silver nanoparticles are available for interaction with an analyte or for functionalisation with a receptor which is capable of interacting with an analyte.

In one embodiment a receptor specific to a target analyte is attached to the surface of the nanoparticles.

The receptor may be bonded directly to the surface of the nanoparticles.

In one embodiment a linker is provided between the receptor and the silver nanoparticles.

In one embodiment the linker incorporates an organic or an inorganic functional group. The functional group may comprise a thiol group or an amine group.

More than one type of receptor may be attached to the silver nanoparticles.

In one embodiment the silver nanoparticles are stable, shaped and substantially plate-like in structure.

In a preferred embodiment the silver nanoparticles have dimensions in the range of from 5 to 100 nm. The silver nanoparticles may have dimensions in the range of from 18 nm to 32 nm.

In one embodiment the morphology of at least some of the silver nanoparticles is hexagonal and/or triangular in shape. At least some of the silver nanoparticles may display an SPR peak in the 400 nm region. At least some of the silver nanoparticles may display an SPR peak in the 470 to 600 nm region. At least some of the silver nanoparticles may display an SPR peak in the 340 nm region.

In one case the silver nanoparticles show predominantly non-spherical morphology.

The silver nanoparticles are immobilised on a permeable substrate.

The silver nanoparticles are disposed on a film.

In one embodiment the silver nanoparticles are formed into a predetermined body. The silver nanoparticles may be cast, pressed or moulded into a body.

In one case the nanoparticles are in a solvent system. The solvent system may be an aqueous based system.

In another aspect the invention provides a method for detecting an analyte comprising contacting the analyte with a sensor of the invention and observing a detectable change. The detectable change may be a change in the absorption spectrum. The detectable change may be a qualitative or quantitative change.

In one case the change is a colour change observable with the naked eye.

In one embodiment the change in the absorption spectrum is a shift which is detected in the range from 200 nm to 900 nm. The shift is preferably from 1 to 150 nm. The shift may be from 5 to 50 nm.

In another aspect the invention provides a method for preparing silver nanoparticles which comprises the step of forming the nanoparticles in the presence of a polymeric stabiliser.

In one embodiment the method comprises the step of controlling the optical response of the silver nanoparticles by varying the concentration of the polymeric stabiliser.

In one embodiment the polymeric stabiliser has a molecular weight of greater than 10 kDa. The molecular weight of the polymeric stabiliser may be less than 1300 kDa.

In one case the polymeric stabiliser is water soluble.

The polymeric stabiliser is selected from one or more of polyvinyl alcohol), poly(vinylpyrollidone), poly(ethylene glycol), and poly(acrylic acid).

In one case the polymeric stabiliser is poly(vinyl alcohol).

In one embodiment the method comprises reducing a silver salt. The silver salt may be silver nitrate.

In one embodiment the reaction is carried out in the presence of seed silver nanoparticles.

Preferably the reaction is carried out in the presence of seed silver nanoparticles. The ratio of [silver nitrate] to [silver seed] may be greater than or equal to 50:1.

In one embodiment the ratio of [silver nitrate] to [silver seed] is between 50:1 and 200:1. Typically the ratio of [silver nitrate] to [silver seed] is between 50:1 and 100:1.

In one embodiment the reaction is carried out in an aqueous medium.

The reduction may be carried out at a temperature of from 10° C. to 60° C., typically the reduction is carried out at a temperature of about 40° C.

The reaction is carried out in the dark, or the reaction may carried out in ambient light conditions, or the reaction may be carried out under controlled irradiation conditions.

The invention also provides nanoparticles when made by the method of the invention. These may be used for example in a sensor as hereindescribed.

In a further aspect the invention provides silver nanoparticles wherein the nanoparticles are between 5 and 100 nm in size. The particles may show predominantly non-spherical morphology.

In one case the nanoparticles are between 10 and 50 mm in size.

In another case the nanoparticles have an average size of 31 nm±8 nm.

In another case the nanoparticles have an average size of 20 nm±8 nm.

In another case the nanoparticles have an average size of 22 nm±8 nm.

The invention also provides the use of silver nanoparticles in any one or more of sensing, biosensing, imaging, data storage, catalysis.

BRIEF DESCRIPTION OF THE DRAWINGS

The invention will be more clearly understood from the following description of some embodiments thereof, given by way of example only with reference to the accompanying drawings in which.

DETAILED DESCRIPTION

Figure 1A:
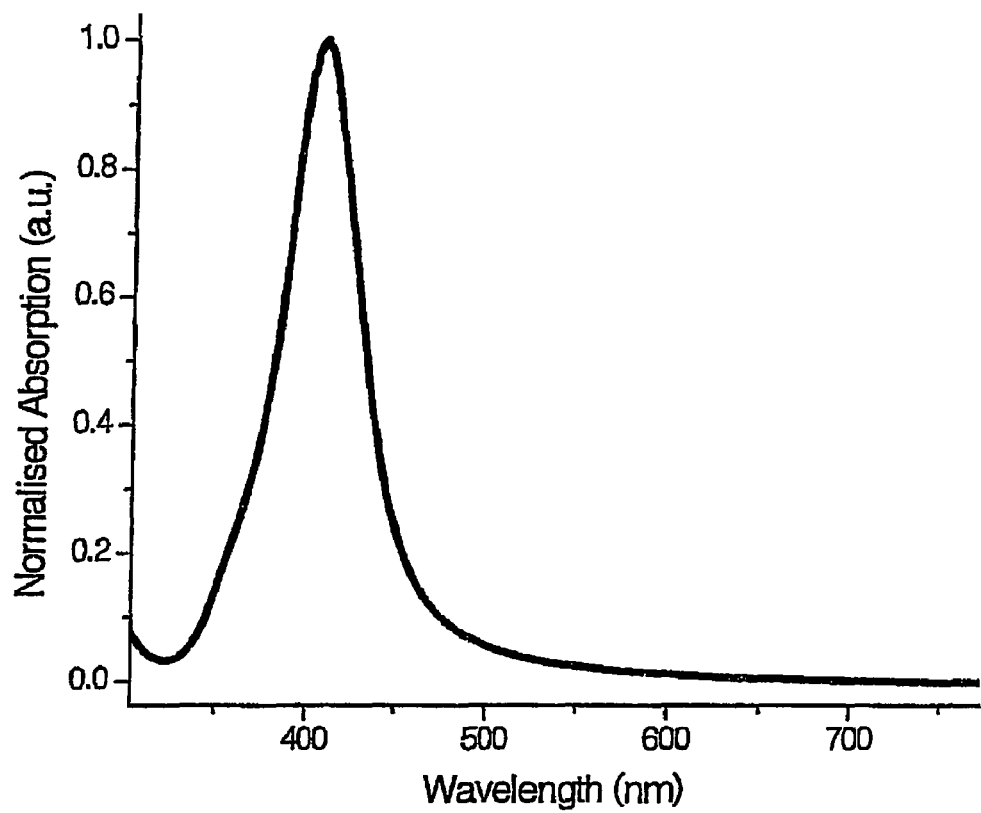
FIG. 1(a) shows a typical UV-visible absorption spectrum (hereinafter, 'spectrum') of spherical nanoparticles having a surface plasmon resonance (SPR) maximum absorption around 408 nm and being yellow in colour.

The invention provides a sensor comprising silver nanoparticles for detecting an analyte.

The invention also provides a sensor comprising silver nanoparticles having a detection means attached thereto wherein the silver nanoparticles provide a detectable change in their U-visible absorption spectrum in response to the binding of an analyte. This change may be observed by instrument or by the naked eye.

Metal nanoparticles are small enough to interact intimately with biological or chemical species. Such interaction is facilitated by their comparable size and by the large surface area to volume ratio of the nanoparticles. Molecular species can be readily attached to the nanoparticle surface. The attachment, which can be by non-specific adsorption or interactions involving covalent or electrostatic bonding, affects the SPR of the nanoparticle and alters the spectral response. This alteration of the spectral response can be observed either as a wavelength shift in spectral peak, a diminishment or enhancement of the peak absorbance, or a combination of these. This sensitivity of the surface of these nanoparticles to the molecules in the surrounding environment makes them ideal for sensor applications.

Metal nanoparticles that differ in size, shape and composition scatter light of different wavelengths according to their distinct SPR. This is again due to the influence of these factors on the spectral response of the SPR. The most typical metal nanoparticle shape is spherical and these have a characteristic single SPR spectral peak. If a metal nanoparticle has a non-spherical shape, for example ovoid, then the SPR will exhibit more than one peak. This occurs as the nanoparticles are no longer isometric and the SPR electrons have more than one oscillation axis. In the case of ovoid nanoparticles, electronic oscillation about the major and minor axes will result in at least two peals in the SPR spectrum. An advantage of non-isometric metal nanoparticles is their increased sensitivity, which in part arises from the presence of the additional SPR spectral peals. Since the most energetically favourable nanoparticle morphology is spherical, the additional SPR peaks of non-spherical nanoparticles are therefore extra-sensitive to the local environment, and changes in the spectral profile are more easily observable than in the case of single SPR peak spherical metal nanoparticles.

Silver nanoparticles are preferable to gold. This is due to the stronger and more distinctive SPR spectrum of silver nanoparticles, as may be seen by comparing FIG. 1a with FIG. 3a, meaning that they exhibit a far more sensitive response. However it has not been possible to prepare them in a stable and useable format, until very recently.

The method described herein enables the preparation of a range of silver nanoparticles having various colours and shapes in solution which are stable over long time periods and do not aggregate.

Substantially all of the surfaces of the silver nanoparticles are available for interaction with an analyte or for functionalisation with a receptor which is capable of interacting with an analyte because the nanoparticles can be produced in a solvent based system such as an aqueous medium rather than by a deposition process.

By conducting the preparation in ambient light conditions at temperatures ranging from 4 to 40° C. and stabilizer concentrations ranging from 1% w/v to 5% w/v, it is possible to obtain silver nanoparticles having a variety of colours and sizes. The following varieties are described by way of illustration:

(a) Spherical silver nanoparticles which appear yellow in colour to the naked eye. These particles have an average diameter of 31±9 nm and display a single absorption band, which occurs in the range 410 to 450 nm.

(b) A mixture of spherical and triangular shaped silver nanoparticles which appear red in colour to the naked eye. The average diameter of the spherical particles is 20±8 nm; the average edge length of the triangular particles is 20±8 nm. This mixture of particles displays two absorption bands. One occurs in the range 405 to 420 nm and is associated with the presence of spherical silver nanoparticles. The second band occurs in the range 500 to 530 nm and is associated with the presence of triangular silver nanoparticles.

(c) A mixture of spherical, triangular and hexagonal shaped silver nanoparticles which appear purple in colour to the naked eye. The average diameter of the spherical particles is 22±8 nm, the average edge length of the triangular particles is 22±8 nm and the average distance between opposite faces of the hexagonal particles is also is 22±8 nm. This mixture of particles displays two absorption bands. One occurs in the range 405 to 420 nm and is associated with the presence of spherical silver nanoparticles. The second band occurs in the range 530 to 550 nm and is associated with the presence of triangular and hexagonal silver nanoparticles.

(d) A mixture of spherical and hexagonal shaped silver nanoparticles which appear blue in colour to the naked eye. The average diameter of the spherical particles is 19±4.5 nm; the average distance between opposite faces of the hexagonal particles is also 19±4.5 nm. This mixture of particles displays two absorption bands. One occurs in the range 405 to 420 nm and is associated with the presence of spherical silver nanoparticles. The second band occurs in the range 560 to 600 nm and is associated with the presence of hexagonal silver nanoparticles.

By conducting the preparation at ambient temperature under controlled irradiation conditions using, for example, a xenon lamp, it is possible to obtain a mixture of triangular and hexagonal silver nanoparticles which appear red to the naked eye. The average edge length of the triangular particles is 56±7 nm; the average distance between opposite faces of the hexagonal particles is also 56±7 nm. This mixture of particles displays one absorption band which occurs in the region 490 to 510 nm. By varying the irradiation conditions, particles may be produced consisting of triangular shapes only, hexagonal shapes only or a mixture of triangular and hexagonal shapes, having a single plasmon band which is tuned to occur in the range of about 450 nm to about 650 nm.

By conducting the preparation in the dark at temperatures ranging from 4 to 40° C. and stabilizer concentrations ranging from 1% w/v to 5% w/v, it is possible to obtain silver nanoparticles having a variety of colours and sizes. The following varieties are described by way of illustration:

a) silver nanoparticles which appear orange to the naked eye. These particles display a single plasmon band, which occurs around 480 nm.

b) Orange silver nanoparticles. This sample contains spherical silver nanoparticles and truncated triangular nanodisks of silver. The average size of these particles is 27±5.5 nm. This sample displays two plasmon bands. The first band occurs in 410 to 420 nm region. The second band occurs in the 470 to 490 nm region.

c) Blue silver nanoparticles. The morphology and size of the nanoparticles in this sample is still to be determined. This sample displays two plasmon bands. The first band occurs in 410 to 420 nm region. The second band occurs in 570 to 600 nm region.

It will be noted that the method can be tuned to produced nanoparticles of a narrow size distribution with various shapes. The advantage of a narrow size distribution is that the band width of the absorption spectrum will also be narrow, for example 50 mm to 100 mm rather than 300 mm or greater for a large size distribution. This narrow size distribution will make it easier to read the SPR response, makes the colour change more distinctive and observable, thus an effective and efficient sensor or assay systems can be made using the nanoparticles of the invention.

The silver nanoparticles may be stabilized by polymeric stabilizers of a range of molecular weights greater than 10 kD and less than 1300 kD. The silver nanoparticles may be stabilized by a range of water-soluble polymeric stabilizing agents including but not restricted to poly(vinyl alcohol) (PVA), poly(vinylpyrollidone) (PVP), poly(ethylene glycol) (PEG), or poly(acrylic acid) (PAA). Preferably, the stabilizer used to prepare the silver nanoparticles is PVA; most preferably, the stabilizer is PVA having molecular weight ranging from 89 kD to 98 kD.

The molar ratio of silver ion to silver seeds influences the final size of the nanoparticles. The appearance of the cornered particles is only observable above a certain nanoparticle size (c. 20 nm). Silver nanoparticles may be prepared using a ratio of ion to seeds ranging from 10:1 to 400:1, more preferably 50:1 to 400:1 and most preferably 100:1. The higher the ratio of ion to seeds, the larger the nanoparticle size obtained.

Figure 1B:
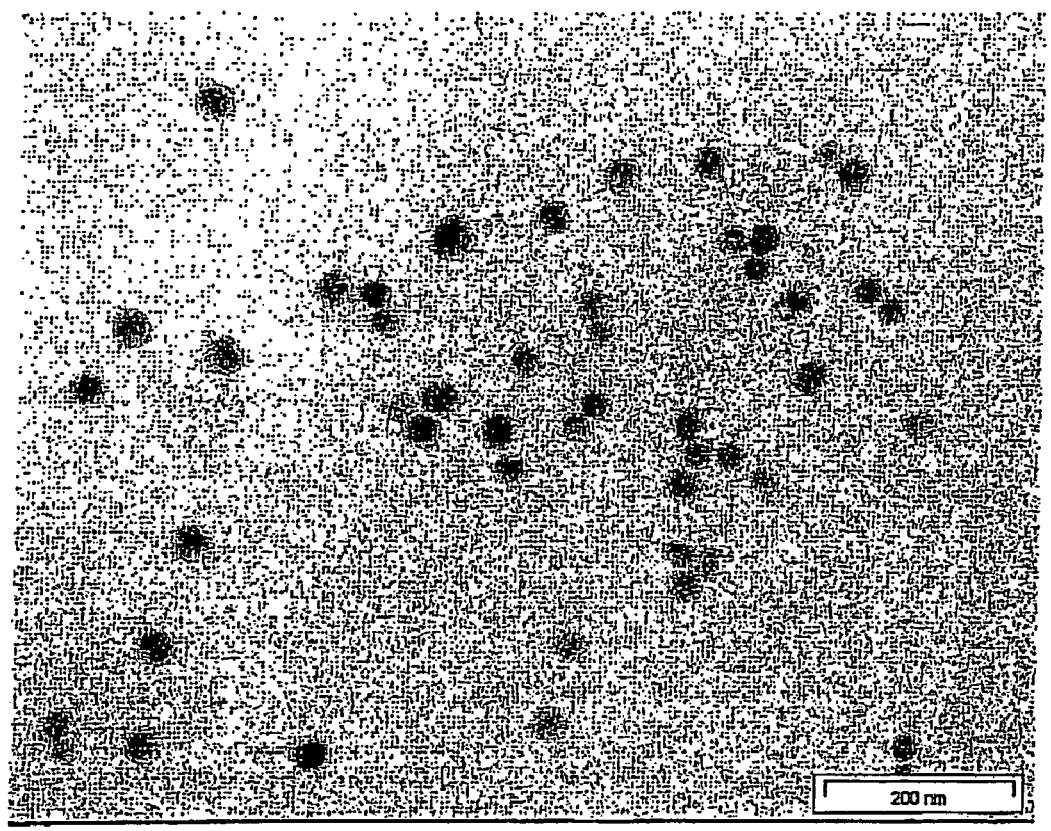
FIG. 1(b) is a transmission electron micrograph (TEM) of the spherical nanoparticles of FIG. 1(a)
Figure 2A:
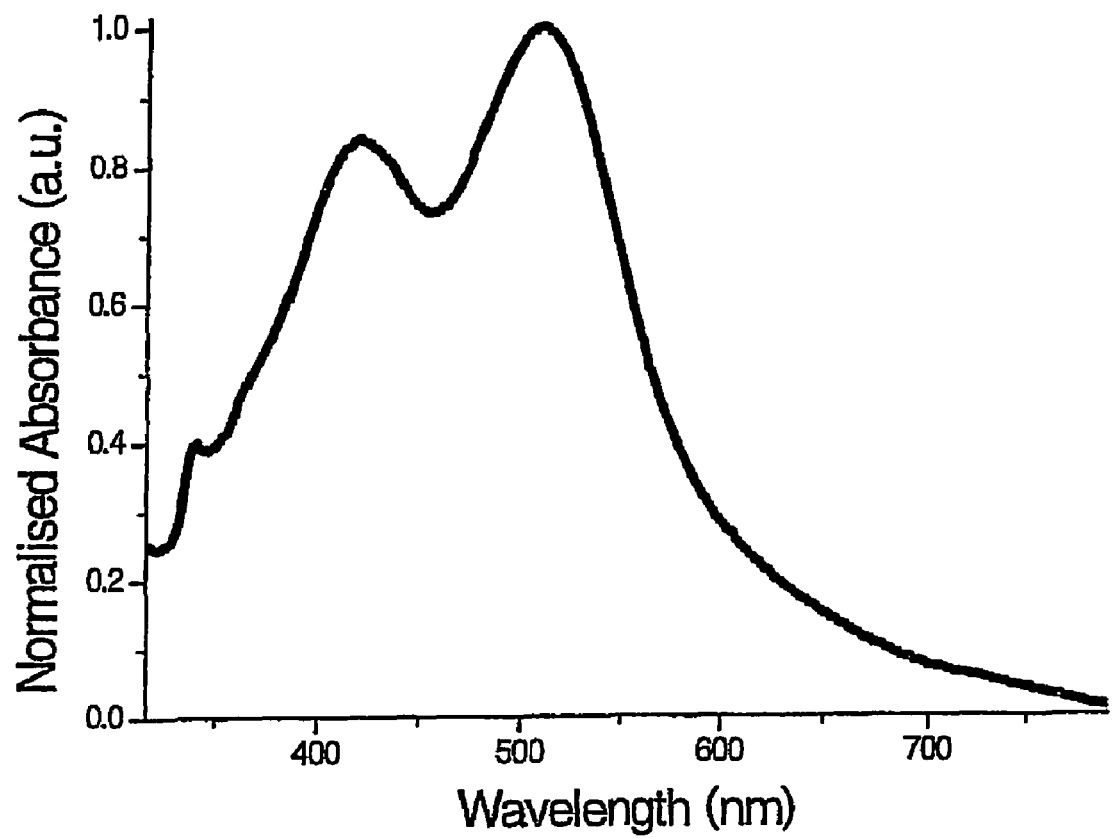
FIG. 2(a) shows a typical spectrum for a mixture of nanoparticles which is red in colour and contains a mixture of spherical and triangular and hexagonal shaped nanoparticles. The SPR maxima are located around 419 nm and 509 nm.
Figure 2B:
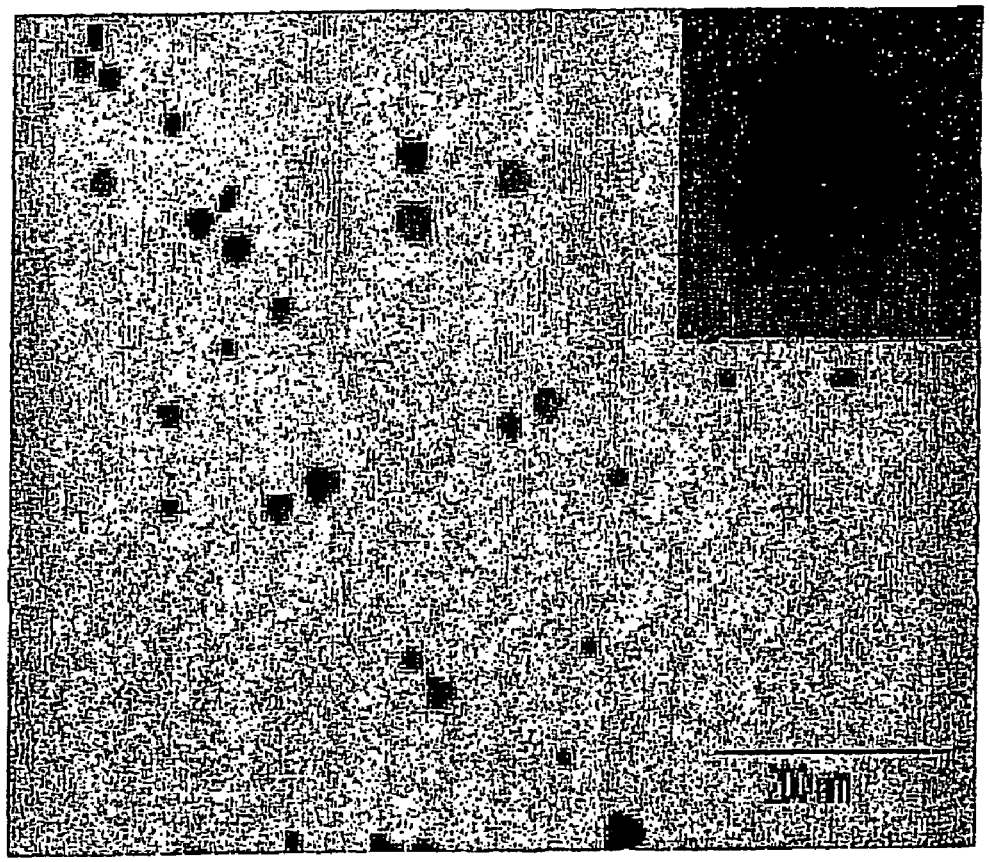
FIG. 2(b) is a TEM of the mixture of nanoparticles of FIG. 2a having spherical, triangular and hexagonal morphologies.

FIGS. 1a and 1b relate to spherical nanoparticles only. FIGS. 2a and 2b relate to a mixture of spherical, triangular and hexagonal nanoparticles. Using nanoparticles which are a mixture of spheres and cornered nanoparticles is useful since the cornered nanoparticles are more sensitive than the spherical ones. The ratio of the changes induced in SPR peaks of the two types of nanoparticles can provide important information for sensing.

Figure 3A:
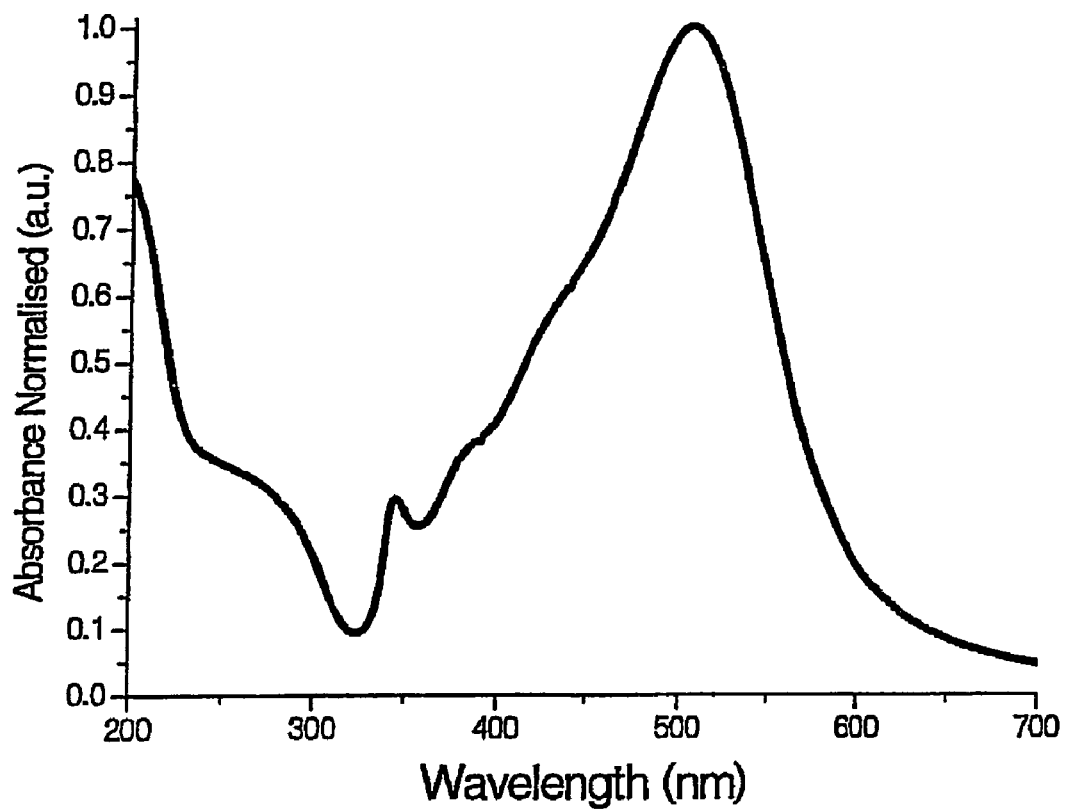
FIG. 3(a) shows a typical spectrum for a mixture of silver nanoparticles having only biangular and hexagonal morphologies, having an SPR peak at 498 nm and being red in colour.
Figure 3B:
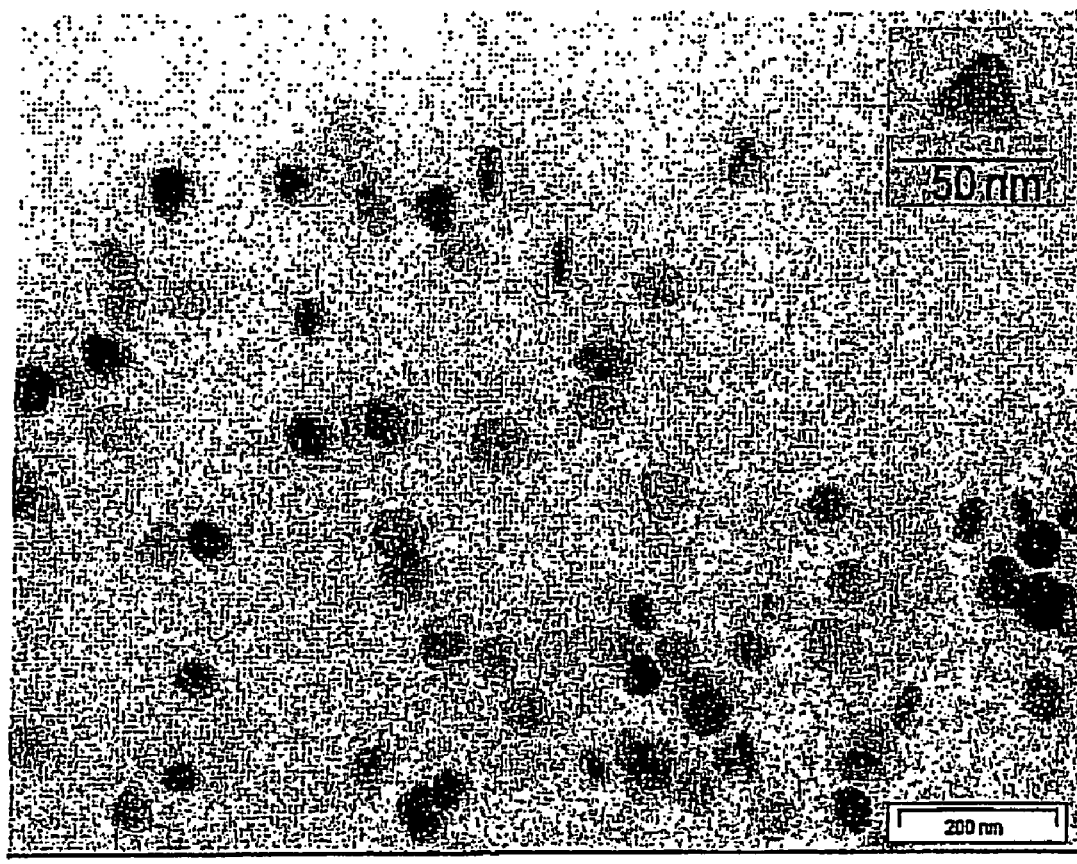
FIG. 3(b) is a TEM of the mixture of triangular and hexagonal nanoparticles of FIG. 3(a)

FIGS. 3(a) and 3(b) relate to triangular and hexagonal nanoparticles only. The absence of a peak in the 410 nm region indicates the absence of spherical nanoparticles as is confirmed by the TEM image in FIG. 3(b). Ambient light of increased intensity from a solar lamp source, was used in the preparation of these nanoparticles. These cornered nanoparticles are especially advantageous due to their very high sensitivity.

Figure 4A:
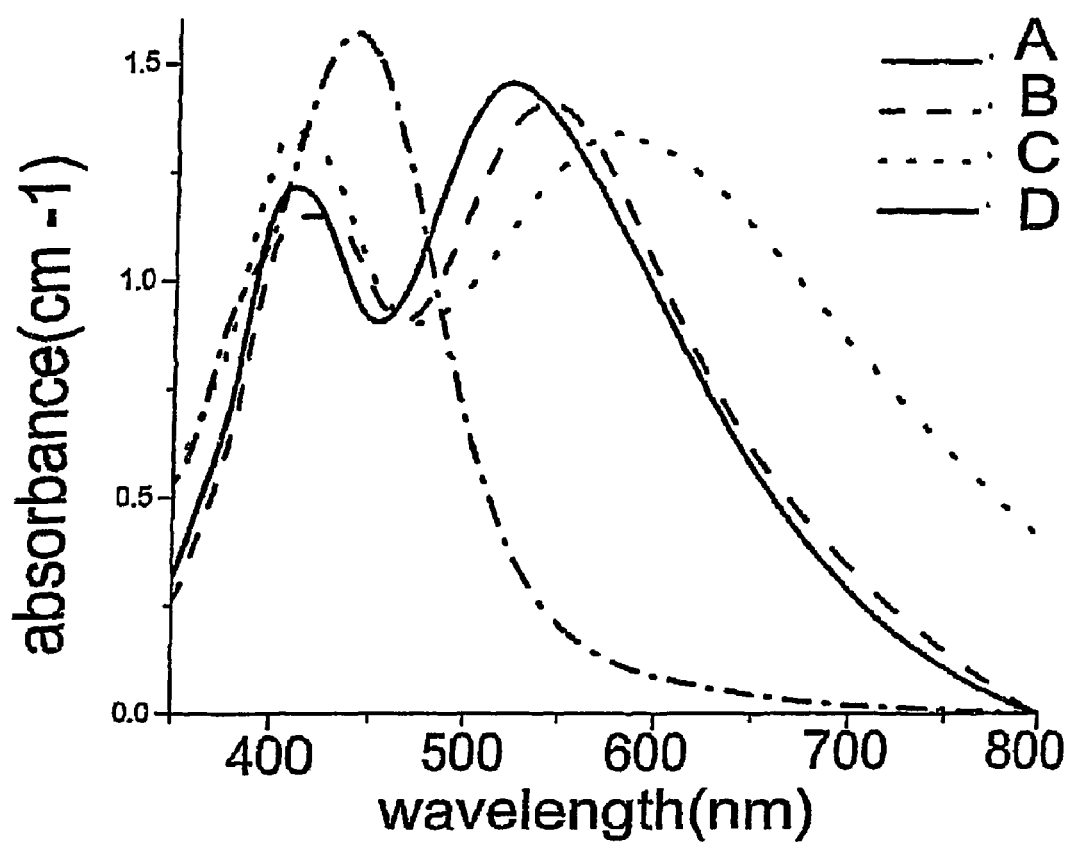
FIG. 4(a) shows typical spectra of batches of silver nanoparticle samples prepared under varying reaction conditions illustrating a variation in the position of the second plasmon band depending on the choice of reaction conditions. Spectrum A is associated with triangular nanoparticles which appear red in colour to the naked eye. Spectrum B is associated with a mixture of triangular and hexagonal nanoparticles which appear purple in colour. Spectrum C is associated with hexagonal nanoparticles which appear blue in colour. Spectrum D is associated with spherical nanoparticles which appear yellow in colour.
Figure 4B:
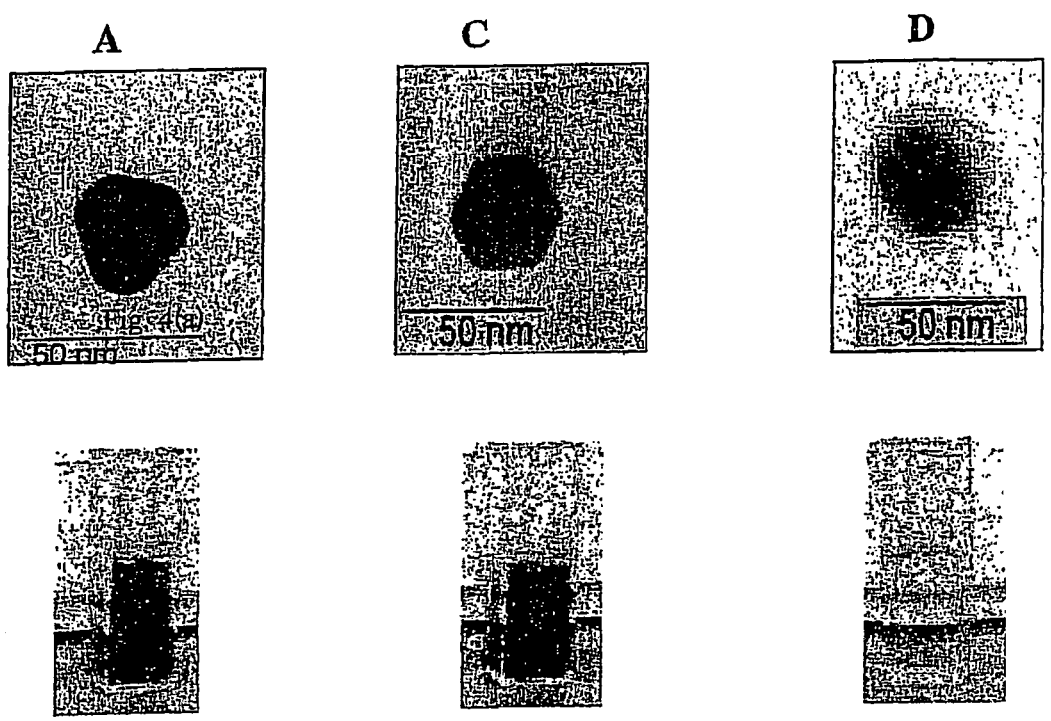
FIG. 4(b) shows TEM of the predominant nanoparticle shape associated with the absorption spectra shown in FIG. 4(a)

FIG. 4(a) shows spectra of nanoparticles produced by the synthetic method of the invention demonstrating that this method can be used to prepare silver nanoparticles of a variety of colours, ranging from red to purple to blue. This is carried out through variation of the reaction conditions; particularly the concentration of stabilising agent used. This allows of the position of the long wavelength SPR band to be tuned. The SPR band position is dependent on the predominant nanoparticle shapes present in a sample. FIG. 4(b) illustrates the predominant nanoparticle morphology associated with each sample in FIG. 4(a).

In contrast to other methods reported for the generation of shaped silver nanoparticles, in the method of the invention, the formation of silver nanoparticles, both spherical and non-spherical is not a photo-induced process and does not rely on light for the generation of the silver nanoparticles. This is demonstrated in FIG. 5 which shows a spectrum of silver nanoparticles of spherical and truncated triangular morphology which were prepared in the absence of irradiation and ambient light. The silver nanoparticles of FIG. 5 were prepared by carrying out the reaction in a darkroom.

Alternative Nanoparticle Synthesis

Figure 6A:
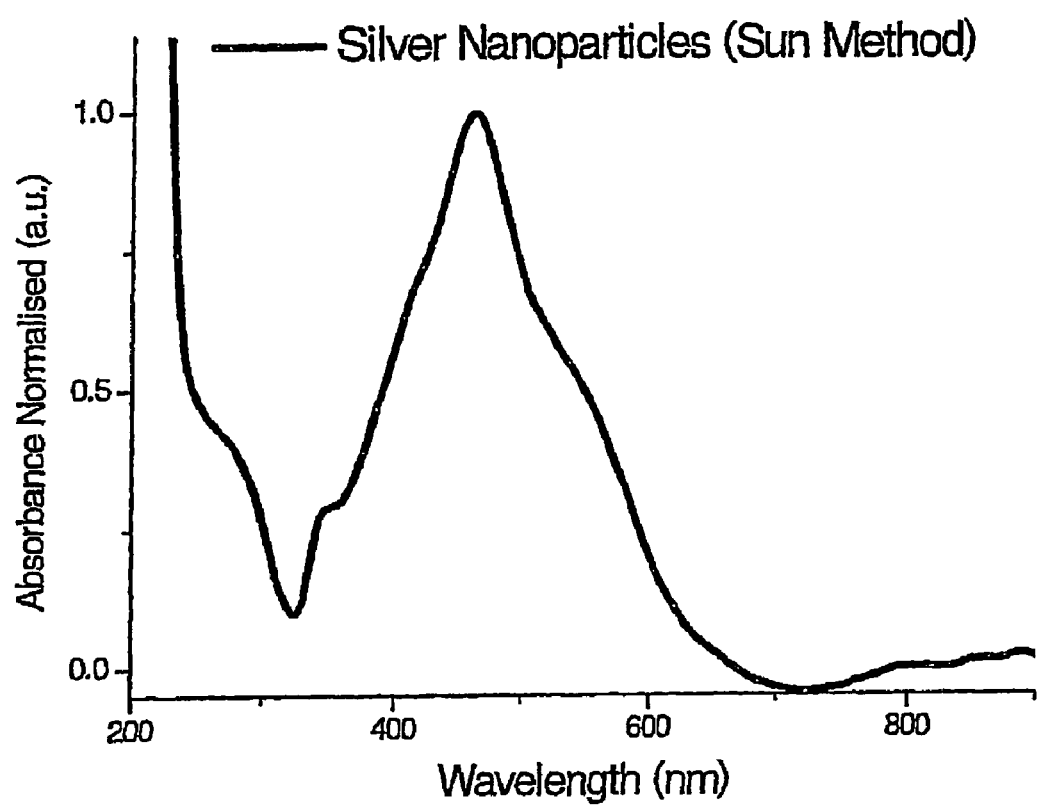
FIG. 6(a) a typical spectrum of silver nanoparticles produced according to the method described by Sun et al; (16)

Silver nanoparticles were also prepared by an alternative method as described by Sun et al [16]. This method requires a length reflux period of greater than 10 hours. The spectrum of the silver nanoparticles as shown in FIG. 6(a), shows main peak at 463 nm with a second feature in the region of 347 nm which is typically expected of silver triangular nanoplates. The TEM shown in FIG. 6(b), confirms the presence of shaped nanoparticles, including triangles and hexagonal morphologies. In contrast to the silver nanoparticles produced by the method described herein, the nanoparticles produced by the Sun method show a wide dispersion of sizes with nanoparticle diameters ranging from about 10 nm to larger than 100 nm observed in the same sample. A significant degree of aggregation is also observable in the TEM image, which is considered as disadvantageous property of nanoparticles. This is again in contrast to the silver nanoparticles produce by the method described herein.

Figure 10:
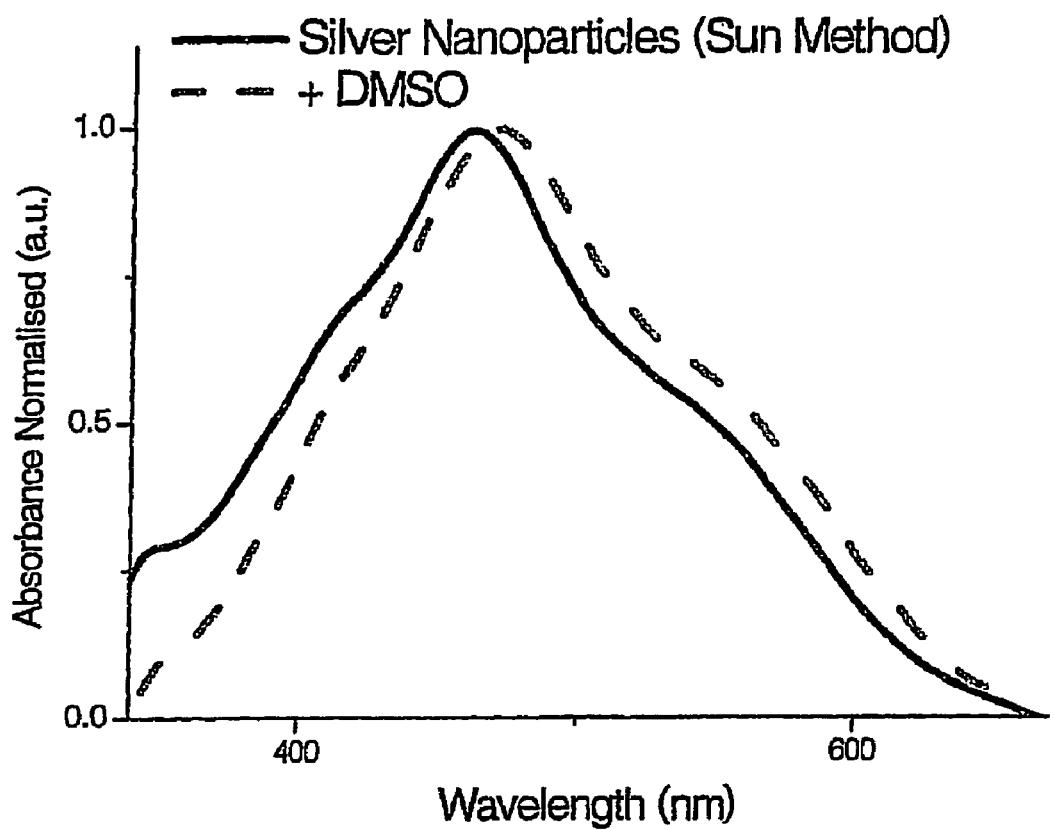
FIG. 10 shows a spectrum of silver nanoparticles produced according to the method of Sun et al which undergoes a spectral shift of 6 nm upon addition of DMSO.

In FIG. 10 the SPR response of the silver nanoparticles produced by the Sun method is demonstrated. On addition of DMSO a 6 nm shift to longer wavelengths is observed in a similar manner to that which occurs in the case of the silver nanoparticles produced by the method described here in. Hence, the SPR response is also given by silver nanoparticles produced by alternative methods and hence that such silver nanoparticles may also be used for sensing purposes.

Figure 8:
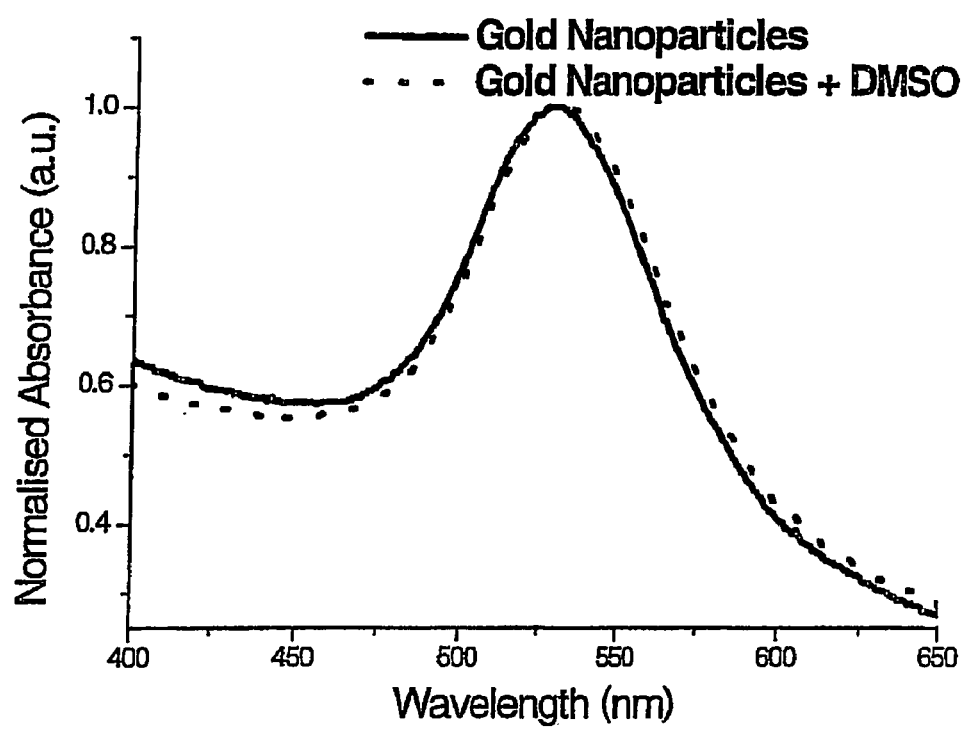
FIG. 8 shows a typical spectrum of gold nanoparticles which undergoes a spectral shift of 0.5 nm upon addition of dimethyl sulfoxide (DMSO)
Figure 9:
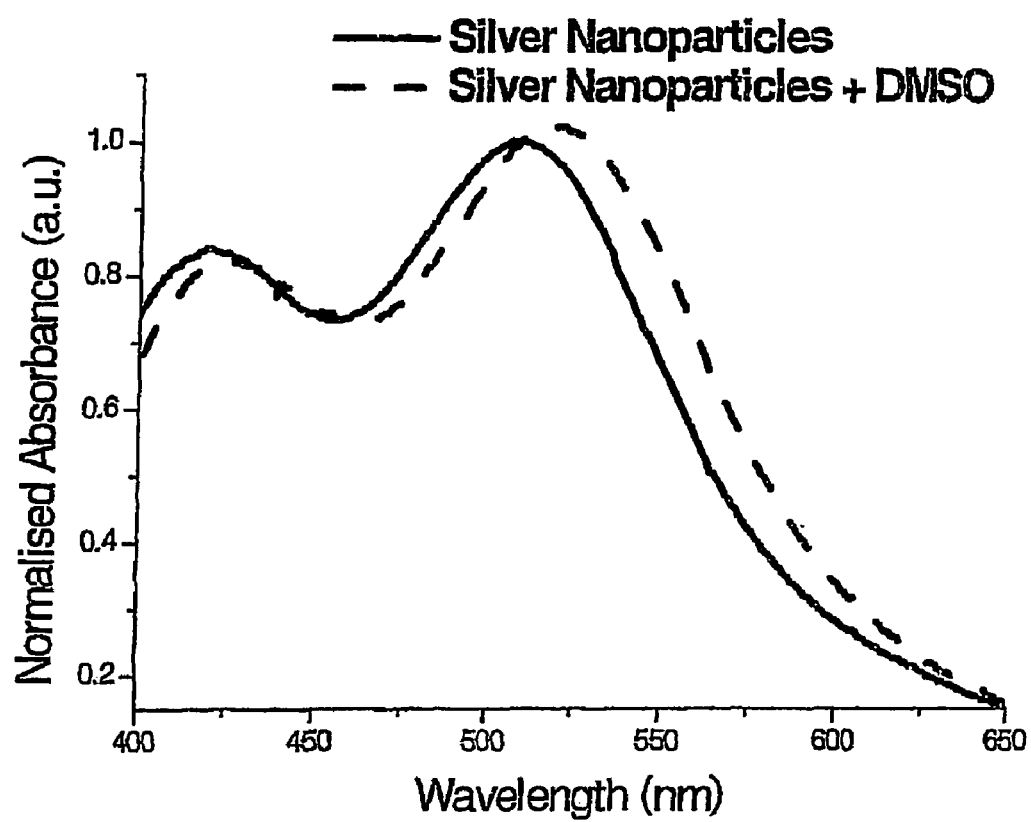
FIG. 9 shows a typical spectrum of silver nanoparticles which undergoes a spectral shift of 11 nm upon addition of DMSO.

FIGS. 8 and 9 demonstrate the enhanced sensitivity of silver nanoparticles over gold nanoparticles. The silver nanoparticles exhibit an 11 nm shift in response to dimethyl sulfoxide (DMSO) whereas a shift of only 0.5 is found in the case of gold.

Figure 11:
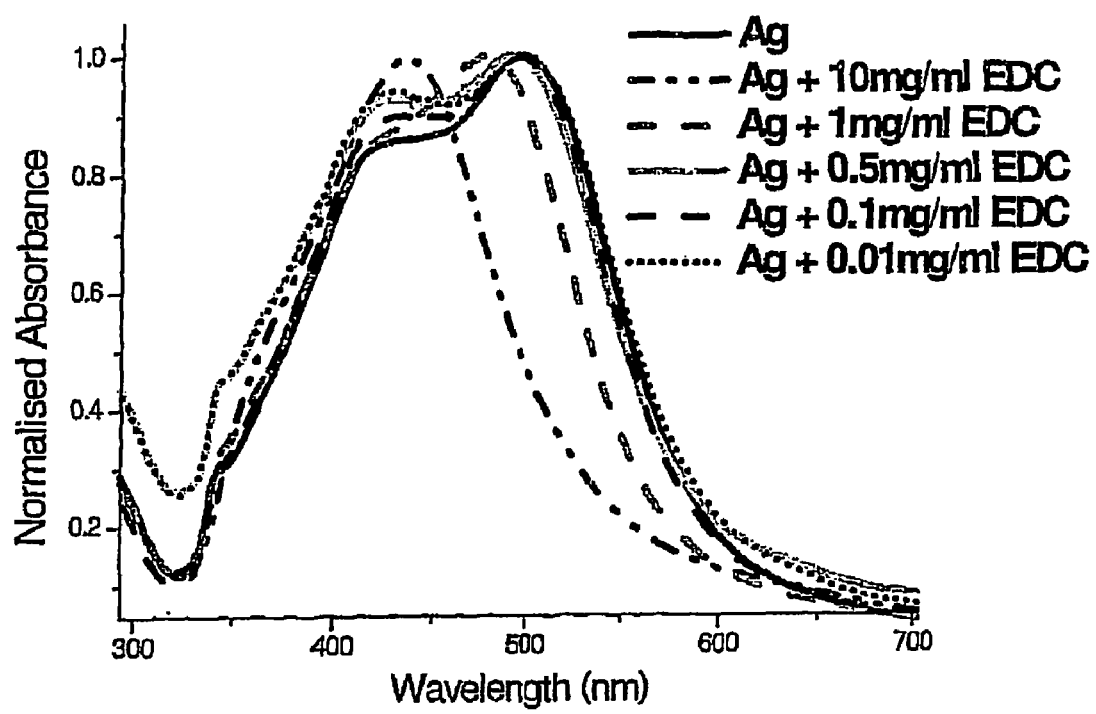
FIG. 11 shows a typical spectrum of a mixture of spherical, triangular and hexagonal silver nanoparticles whose SPR absorption maximum is shifted to shorter wavelengths in response to the presence of 1-ethyl-3-(3-dimethylaminopropyl)-carbodiimide (EDC)

FIG. 11 demonstrates the detection of the molecule N-(3-Dimethylaminopropyl)-N'-ethylcarbodiimide hydrochloride (EDC) by a silver nanoparticle based sensor of the invention. An SPR response to EDC was observed in the concentration range 10 µg/ml to 10 mg/ml.

Figure 12:
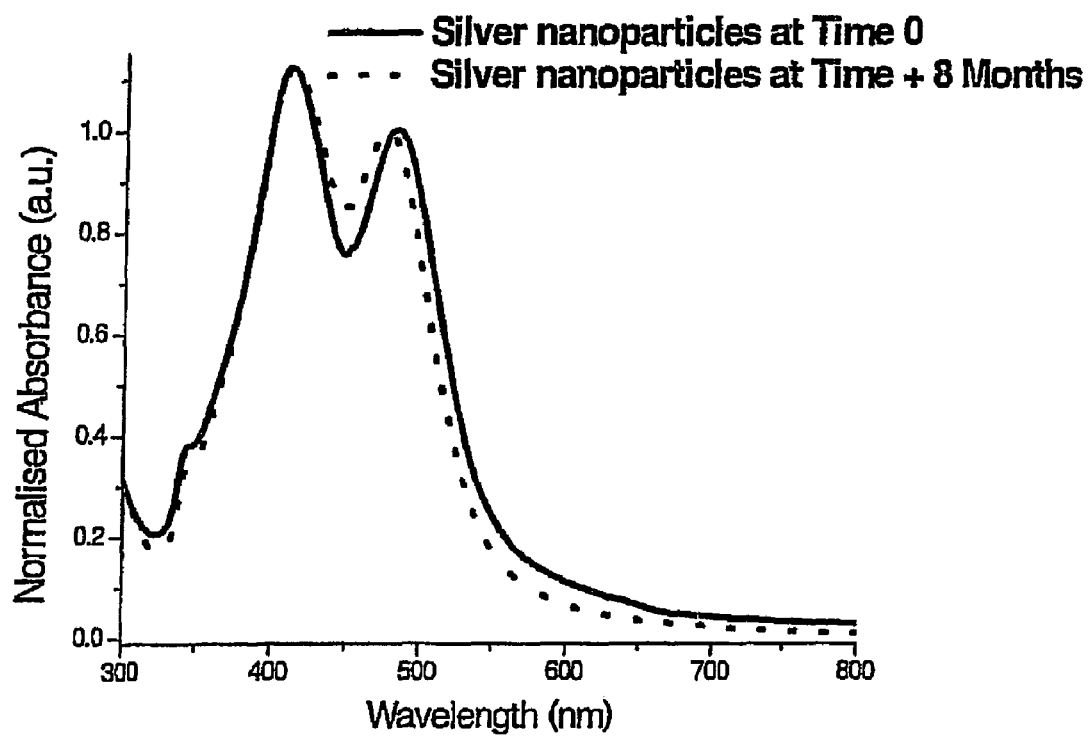
FIG. 12 shows typical spectra of silver nanoparticles at the time of preparation and after 8 months.

The silver nanoparticles of the invention are easily synthesised in a stable form and remain stable over time. The silver nanoparticles are synthesised in solution. The stability of the nanoparticles is illustrated in FIG. 12. Little change is observed in the relative intensity and the profile of the absorption of the plasmon bands after 8 months. A small blue shift of only 5 nm in the position of the peak maximum of the band at 500 nm is found. The lack of aggregation or precipitation of the nanoparticles and the consistency of the spectrum over time, indicates the very high long term stability of the silver nanoparticles of the invention. It is noted that the silver nanoparticles of the invention do not aggregate or exhibit aggregation problems in the manner typically experienced when working with both metallic and non metallic nanoparticles.

Molecular species may be readily attached to the surface of the nanoparticles, for example in the form of a self-assembled monolayer (SAM), and the surface interaction generates a change in the nanoparticles' absorption spectrum. This change may be observed as a colour change visible to the naked eye, or as a shift or change in intensity in the spectrum, and may be used as an indicator in detecting a target analyte.

The ability to easily attach molecular species to the silver nanoparticles makes them ideal for use as a biological, chemical or biochemical sensor. A receptor molecule capable of recognising the target analyte may be attached to the silver nanoparticle surface. Upon interaction with the target molecule, the nanoparticle-receptor system generates a change in the nanoparticles' spectrum which serves to indicate that detection of the target analyte has taken place.

It has been found that using stable silver nanoparticles in a sensor of the invention, the time required to undertake an assay to detect a target analyte is significantly reduced compared to existing diagnostic methods.

Figure 14:
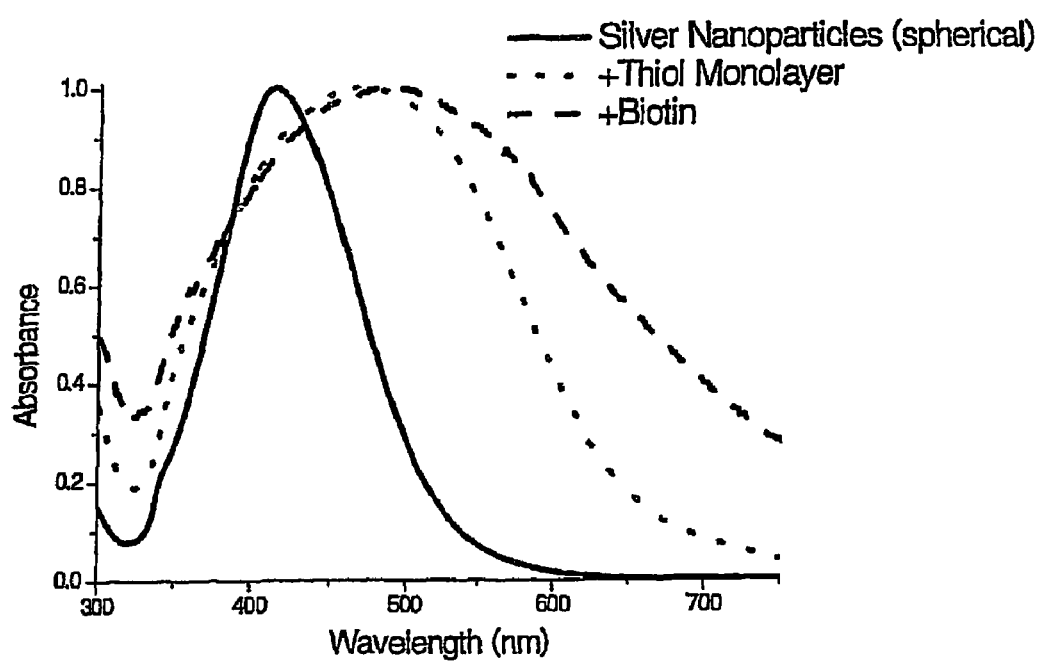
FIG. 14 is a series of normalised spectra recorded at each stage in preparing a sensor of the invention using spherical silver nanoparticles. The spectra of the nanoparticles upon the addition of a thiol layer and after functionalisation with biotin are compared.

Given the inherent ultrafast electronic nature of the silver nanoparticles' SPR, the limiting factor for the rate of detection of the sensor is the rate at which the receptor and analyte interact. Once the receptor and analyte have interacted, the profile of the spectrum obtained, as shown in FIG. 14 (spherical nanoparticles) and FIG. 15(a) (spherical, triangular and hexagonal nanoparticles) for the example of detection of a streptavidin target by a biotin receptor, does not alter over time. In the case of receptor-analyte pairs which do not interact instantaneously, the rate at which the interaction occurs may be determined by observing the change in the spectrum during the course of the interaction.

FIG. 14 shows the attachment of a layer of carboxyl ended thiol molecules (mercaptoundecanoic acid) to spherical silver nanoparticles and the subsequent coupling of amine terminated biotin molecules to the silver nanoparticle surface to form a sensor for streptavidin.

The sensor's response to an analyte is reproducible for concentrations of target analyte over a broad range. A response in the case of streptavidin, is shown in Table 1. Existing methods are sensitive only at low concentrations of analyte. For example ELISAs typically operate at concentration in the range of 1 μg/ml to 200 pg/ml, exceptionally to 10 pg/ml, but are not able to provide reproducible responses outside this range of concentrations. As a result, a pre-treatment stage is usually required in conducting an ELISA and in the case of unknown samples, repeated analysis cycles are frequently required.

The basic construction of the sensor includes a receptor which interacts selectively with a target analyte and an indicator which generates a signal when an interaction has occurred. The silver nanoparticles are used as the indicator component. Any suitable recognition system may be used as the detector and target components. Additionally more than one type of receptor may be attached to the nanoparticles such that the sensor would be capable of detecting more than one target analyte simultaneously.

The well-known bioton-streptavidin interaction was used as an example of a model bio-recognition system. Biotin was used as the receptor, and streptavidin as the target.

Figure 13A:
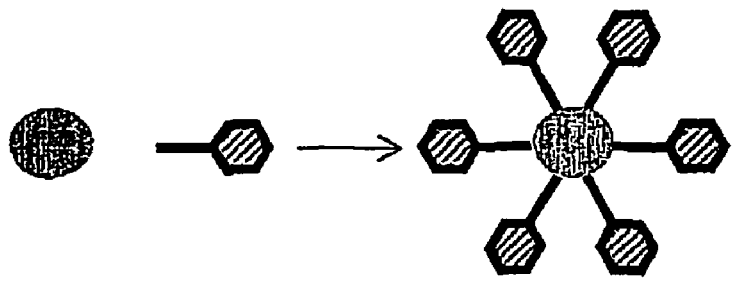
FIG. 13(a) is a schematic representation of a sensor of the invention consisting of silver nanoparticles bearing a receptor (i) and the interaction of the sensor with a target analyte (ii)
Figure 13A:
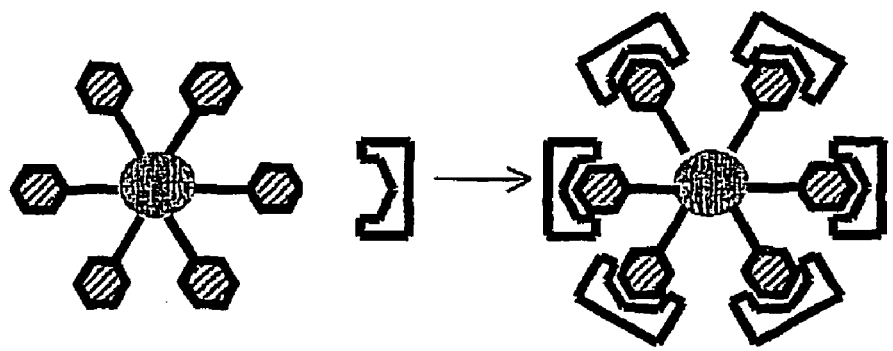
Figure 13A:
Figure 13A:
Figure 13A:

FIG. 13(a) shows the construction of the sensor schematically. The receptor molecule may be attached to the silver nanoparticles via, for example, a thiol or amine group. This group may be part of the receptor molecule's chemical structure or may be introduced through the use of a linker molecule, as follows:

1. An amine-terminated biotin may be attached directly to the silver nanoparticles.
2. In a two-step procedure, a biotin and a thiol may be coupled to each other first prior to attachment to the silver nanoparticles.
3. Using an indirect assembly route, a thiol linker was first attached to the silver nanoparticles. The resulting silver nanoparticles bearing a thiol monolayer were then incubated with biotin solution, resulting in the formation of a biotinylated monolayer on the surface of the silver nanoparticles.

Figure 13B:
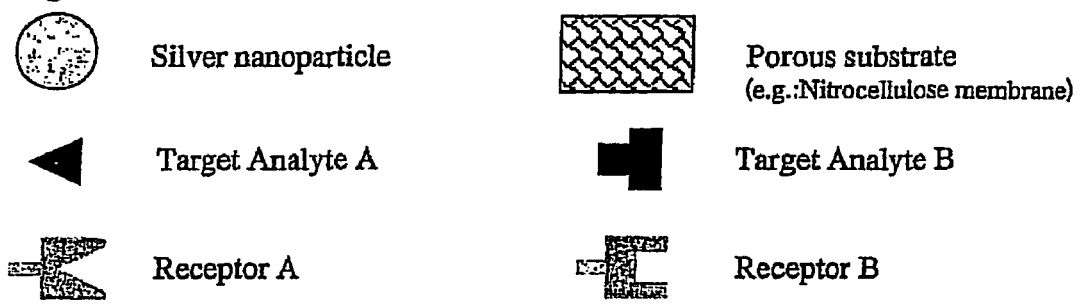
FIG. 13(b) is a schematic representation of a sensor of the invention consisting of silver nanoparticles bearing receptors for two or more target analytes and the interaction of the sensor with the target analytes.
Figure 13B:
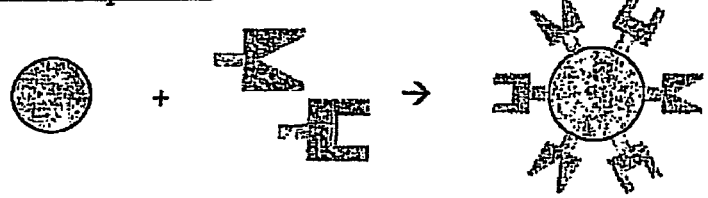
Figure 13B:
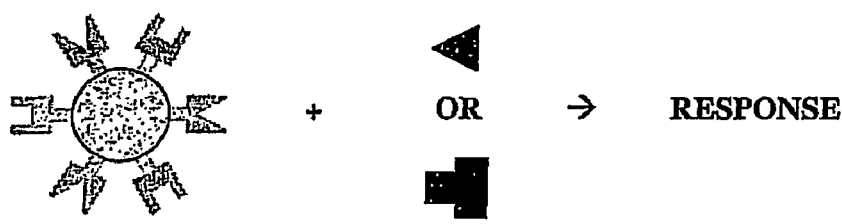
Figure 13C:
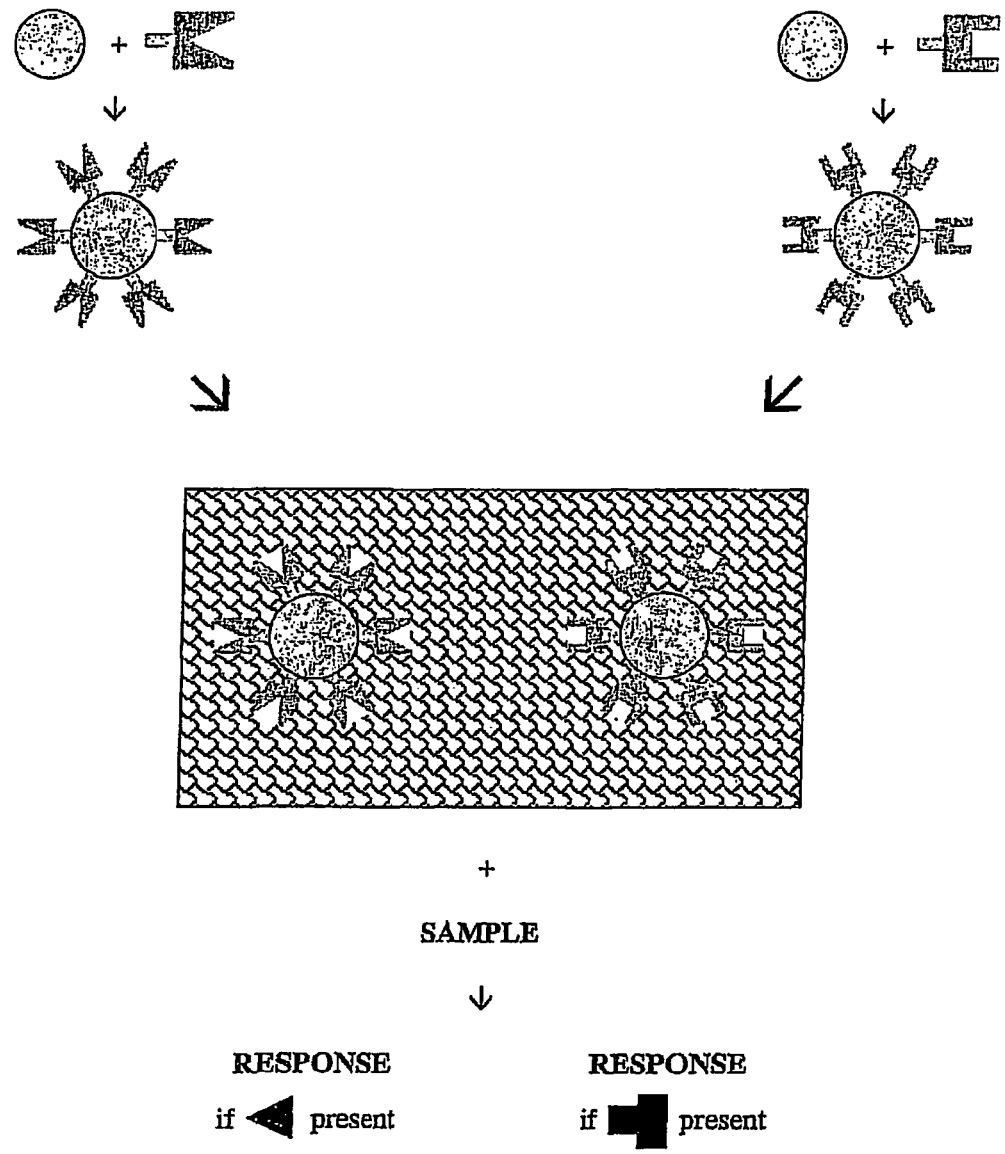
FIG. 13(c) is a schematic representation of a sensor of the invention consisting of two or more batches of silver nanoparticles, each bearing a receptor for a target analyte, immobilised on a permeable solid surface, and the interaction of the sensor with the target analytes.
Figure 13D:
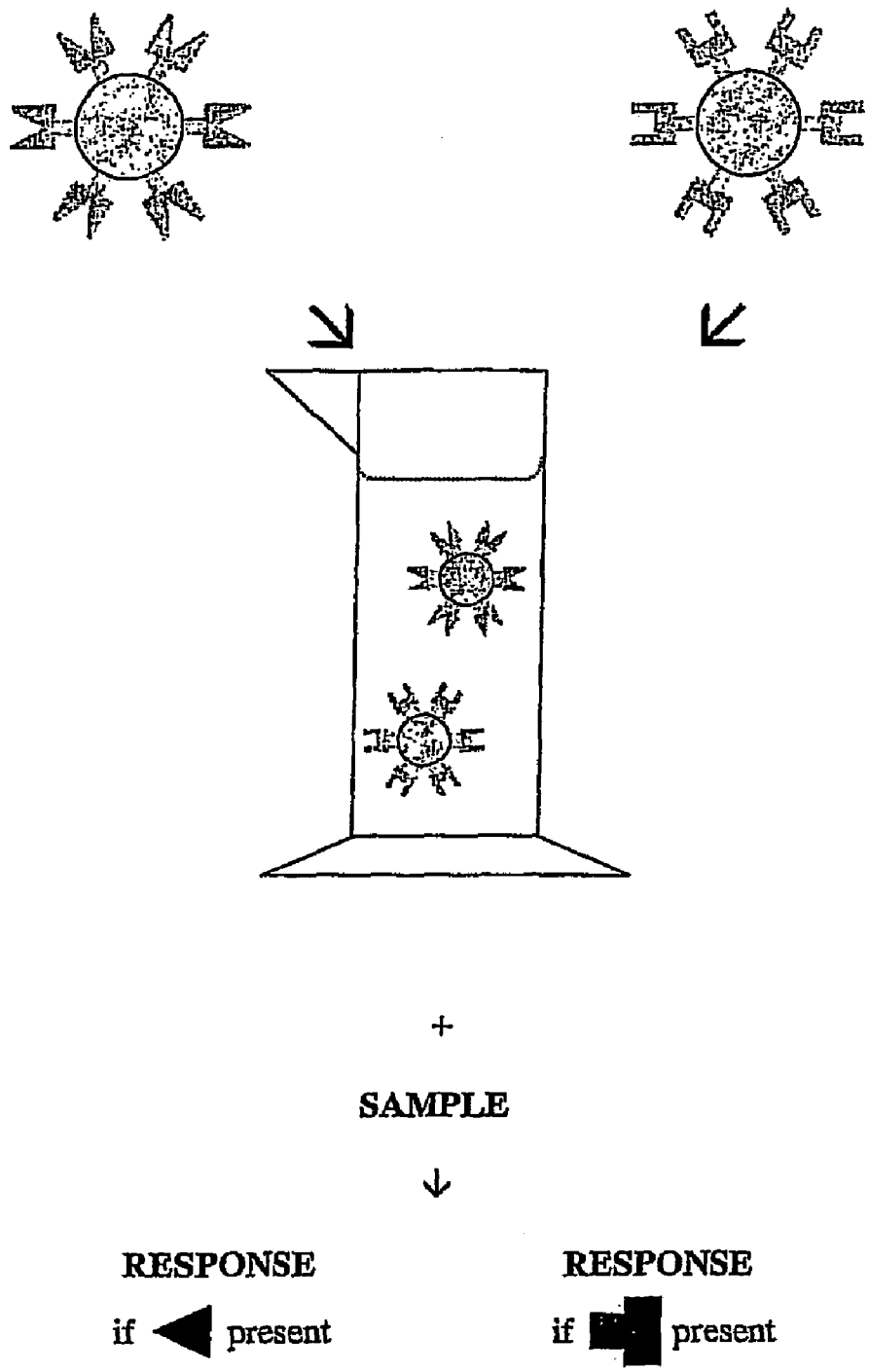
FIG. 13(d) is a schematic representation of a sensor of the invention consisting of two or more batches of silver nanoparticles, each bearing a receptor for a target analyte, in a liquid medium, and the interaction of the sensor with the target analytes.

FIGS. 13(b)-(d) is a schematic showing the construction of a sensor capable of detecting two or more target analytes simultaneously. FIG. 13(b) shows that receptors for two or more target analytes may be deposited on the same batch of nanoparticles. The resulting sensor will generate a response when one or more target analyte is present in the sample matrix. This cannot be achieved at present using gold nanoparticles because the aggregation process responsible for the colour change observed in gold-based assays requires higher concentrations of analyte.

FIG. 13(c) shows that multiple sensors may be prepared, each consisting of a separate batch of nanoparticles with a receptor for a different target analyte deposited on each batch. Each sensor is deposited on the same porous substrate e.g.: nitrocellulose membrane. The sample is applied to each sensor and the response of each sensor to the sample is measured concurrently.

FIG. 13(d) shows the preparation of multiple sensors, each consisting of a separate batch of nanoparticles with a receptor for a different target analyte deposited on each batch such that each sensor thus produced exhibits a discrete absorption peak in the UV-visible spectrum. An aliquot of each sensor is combined into a single solution; upon addition of the sample matrix, the absorption peak for the target analyte(s) present will shift. If one or more target analytes are not present in the sample matrix, no shift will be observed in the peak(s) for their sensor(s).

The advantage of these embodiments of the invention is that they allow for rapid assaying of multiple target analytes and require a minimum quantity of sample.

Figure 6B:
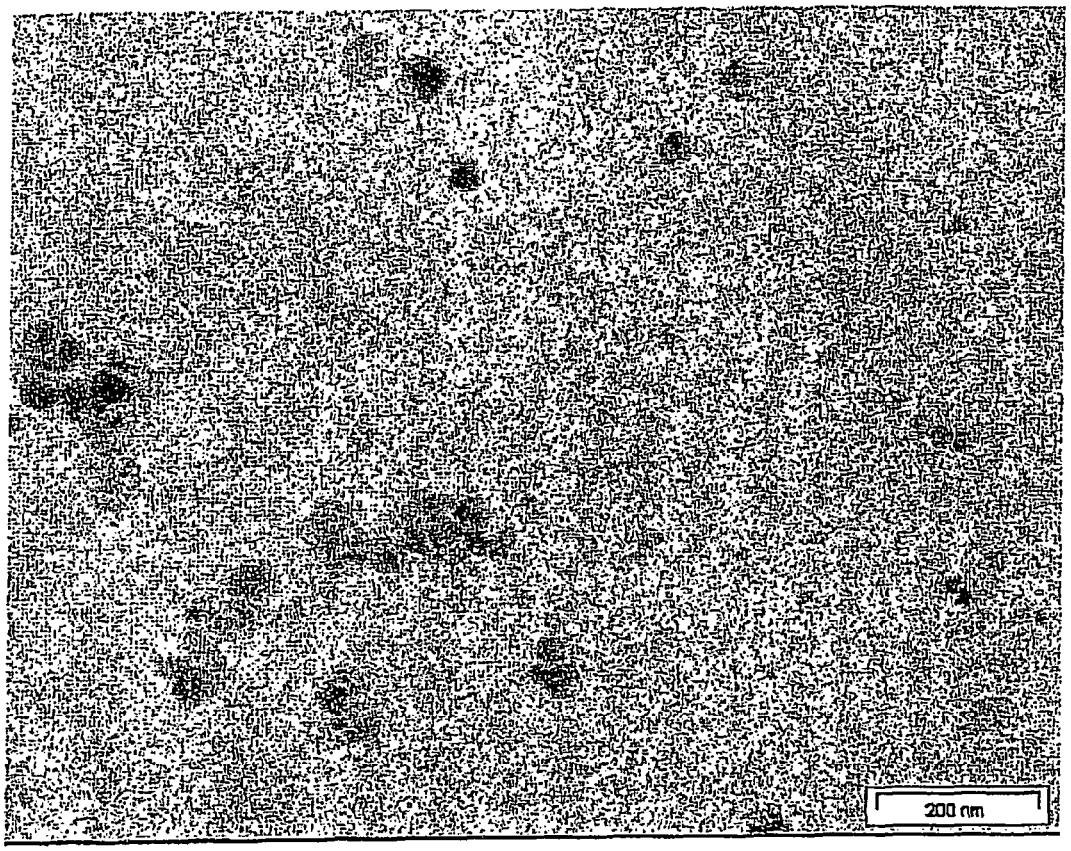
FIG. 6(b) shows TEM of the nanoparticles of FIG. 6(a)
Figure 7:
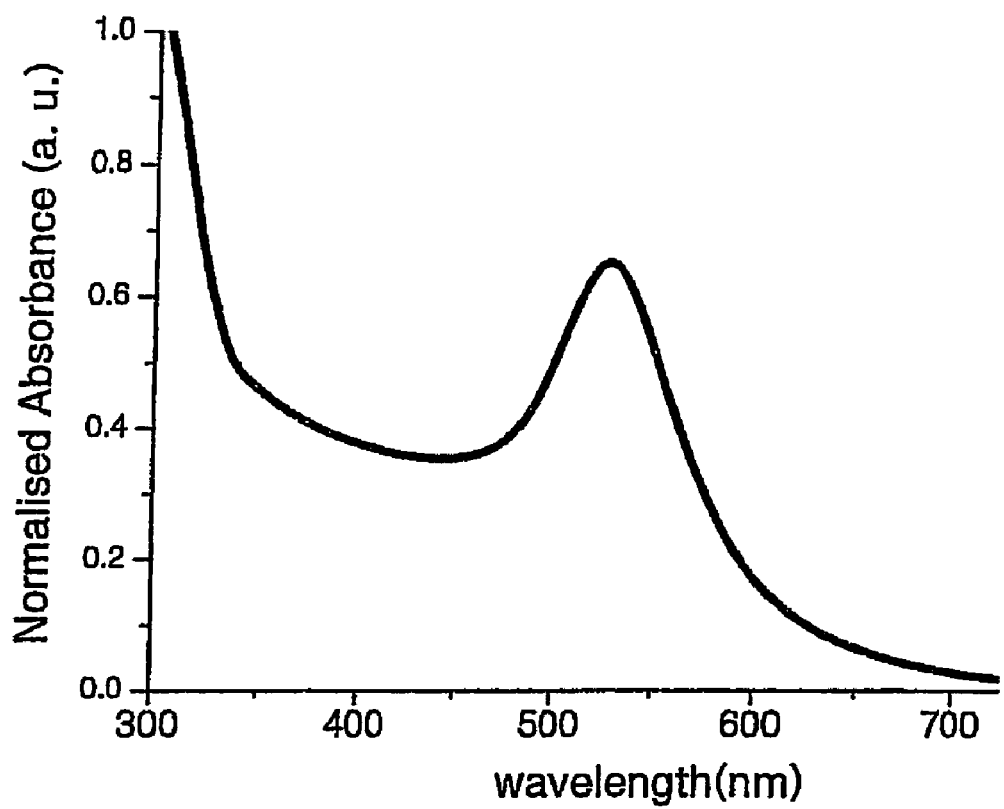
FIG. 7 shows a typical spectrum of gold nanoparticles which are red in colour.

The attachment of the receptor to the silver nanoparticles may be monitored by changes in the spectrum of the nanoparticles, as shown in FIG. 6(b) for the coupling of an amine-terminated biotin to spherical triangular and hexagonal silver nanoparticles.

Figure 15A:
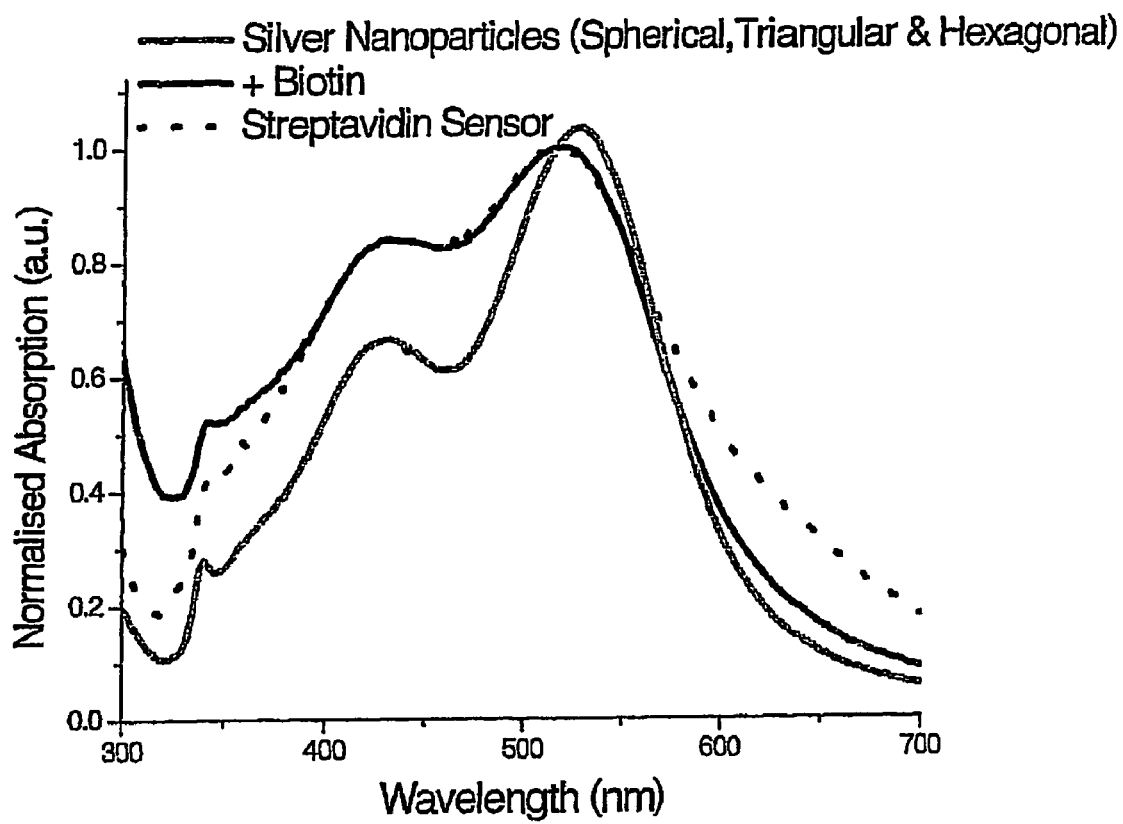
FIG. 15(a) is a series of normalised spectra recorded at each stage in preparing a typical sensor of the invention to detect streptavidin. The spectra of a mixture of spherical, triangular and hexagonal nanoparticles before and after functionalisation with biotin and following centrifuging and resuspension are compared.
Figure 15B:
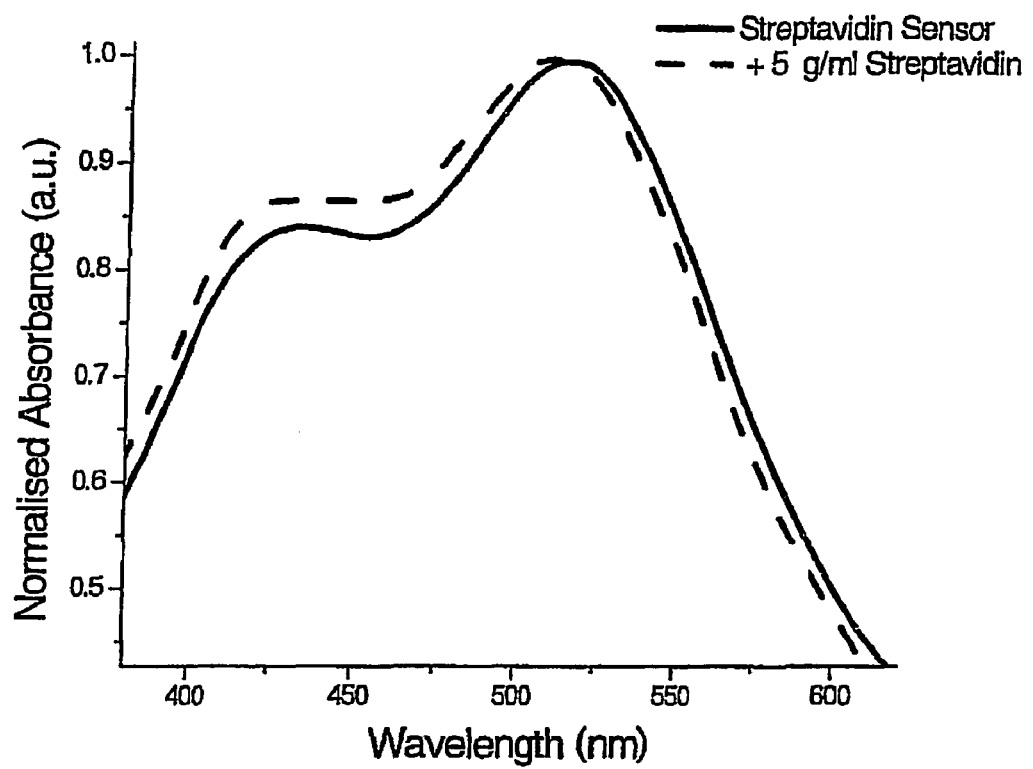
FIG. 15(b) illustrates an SPR shift of 7 nm for the sensor of FIG. 15(a) in response to streptavidin at a concentration of 5 µg/ml.

The biotinylated silver nanoparticles were then reacted with the target molecule, streptavidin. FIG. 14 and FIG. 15(a) show the spectra recorded at each stage in preparing the sensor of the invention for streptavidin using spherical nanoparticles and a mixture of spherical, triangular and hexagonal nanoparticle, respectively; the silver nanoparticles alone, the silver nanoparticles with biotin comprising the streptavidin sensor. In the case of the preparation of the sensor of FIG. 15(a), after biotinylation, the peak at 528 nm in the spectrum is reduced relative to the peak at 428 nm and shifted to longer wavelengths by 12 nm. FIG. 15(b) shows the response of the biotinylated nanoparticles of FIG. 15(a) to streptavidin at a concentration of 5 μg/ml. Reacting the silver with streptavidin leads to a further reduction in the peak at 528 nm relative to the peak at 428 nm and a further shift of 4 ml. The changes observed in these spectra confirm the binding of biotin to the silver nanoparticles to form a sensor, and the subsequent detection of streptavidin by this sensor. After one day, the profile of the spectrum has not changed by comparison to the spectrum recorded at the end of the preparation, showing that the qualitative response of the sensor is stable over time.

Figure 16:
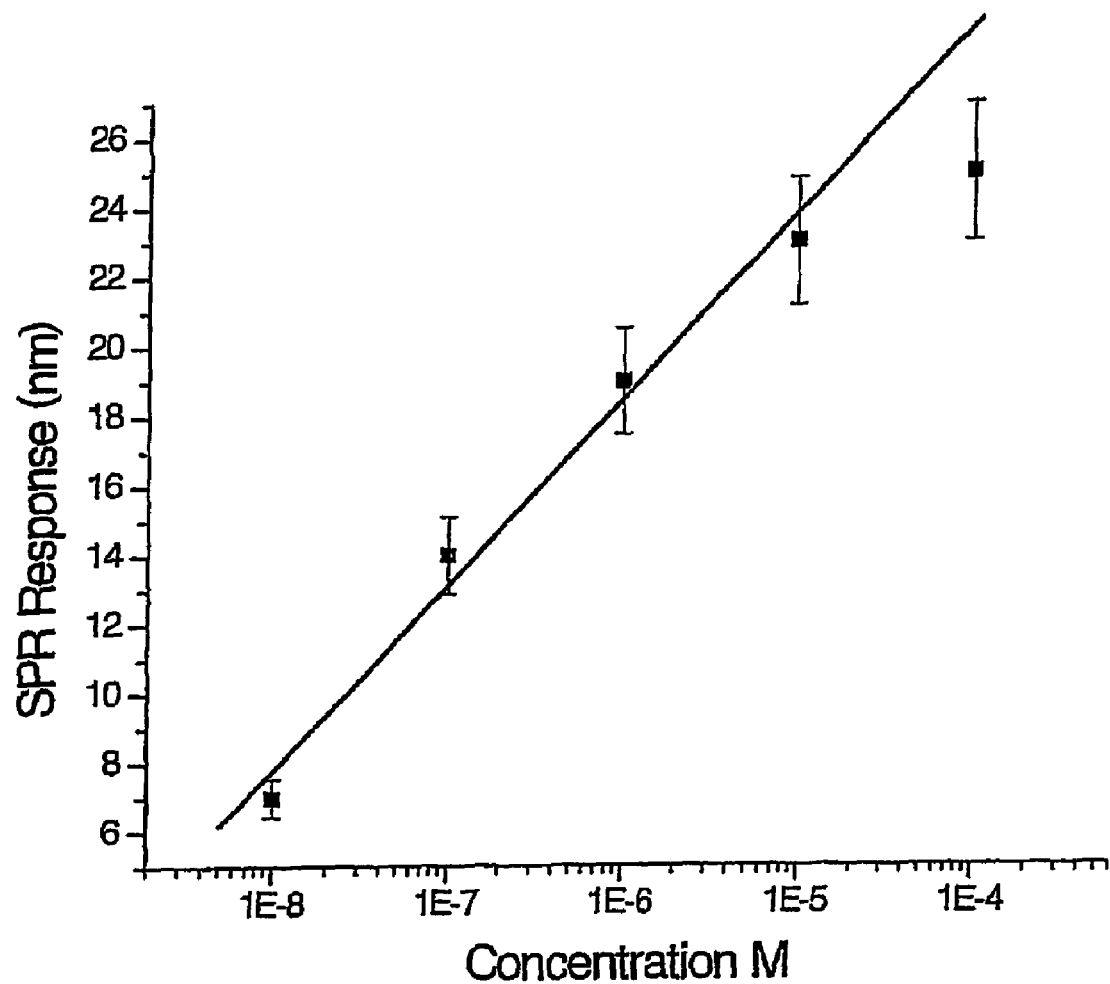
FIG. 16 is a plot of the shift in SPR of another sensor of the invention in response to streptavidin at concentrations ranging from 10 ng/ml to 0.1 mg/ml. A linear fit to the data was obtained in the range 10 ng/ml to 10 µg/ml.

It was found that the sensor of the invention is able to detect a target molecule over a broad range of concentrations. Table 1 shows the response of silver nanoparticles biotinylated with 0.1 mM biotin to form a sensor for streptavidin to concentrations of streptavidin ranging from 0.1 mg/ml to 10 ng/ml. In this case, biotin was used as the receptor, and streptavidin as the target. The response generated by the sensor takes the form of a shift in the SPR maximum absorption in the UV-visible absorption spectrum (SPR Response). FIG. 16 shows a plot of the data in Table 1. The SPR response is found to be proportional to the concentration of the target, showing that the sensor of the invention may be used quantitatively. The linear fit of the data in FIG. 16 indicates the region where this particular sensor of the invention gives a linear response to streptavidin concentrations (0.01 μg/ml to 10 μg/ml) and may be considered as the operational range of this particular sensor. As indicated by the data in FIG. 16, the response of the sensor begins to saturate with concentrations of Streptavidin above 10 μg/ml

TABLE 1

| Streptavidin Sensor | SPR Response (nm) |
|---|---|
| +0.01 μg/ml streptavidin | 7 ± 1 |
| +0.1 μg/ml streptavidin | 14 ± 1 |
| +1 μg/ml streptavidin | 19 ± 1 |
| +10 μg/ml streptavidin | 23 ± 1 |
| +100 μg/ml streptavidin | 25 ± 1 |

Figure 17:
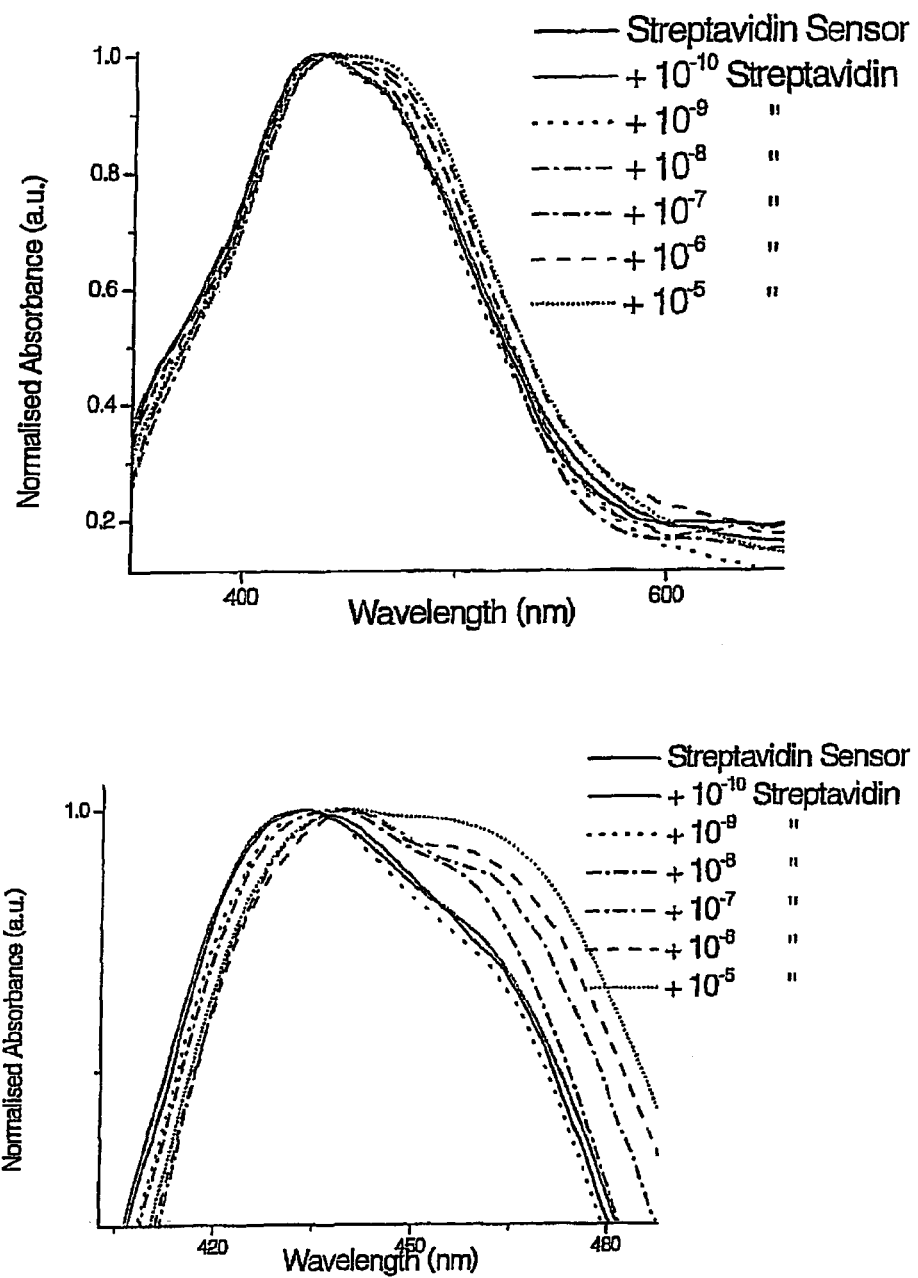
FIG. 17 is a series of normalised spectra showing the response of a typical sensor of the invention to detect streptavidin at concentrations ranging from 100 pg/ml to 0.1 mg/ml. In this particular embodiment of the invention, the qualitative limit of detection for streptavidin is 10 pg/ml; a linear response is obtained in the range 1 ng/ml to 1 µg/ml.
Figure 18:
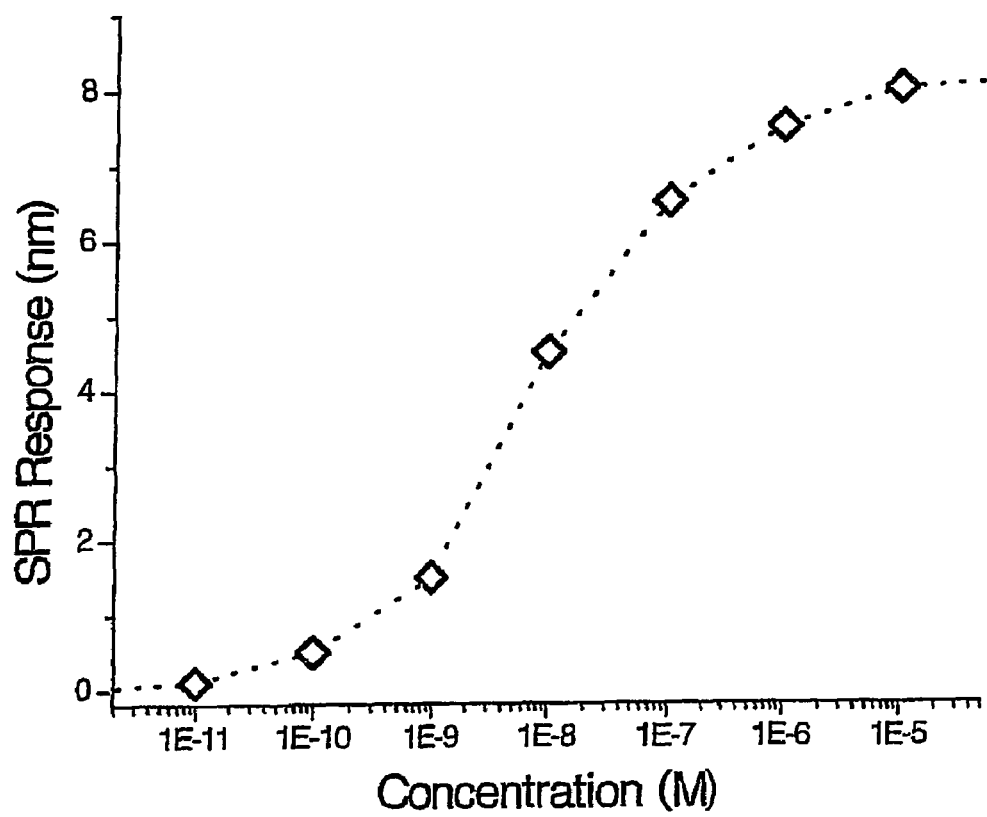
FIG. 18 shows a plot of the shift in SPR of the sensor of FIG. 17 to streptavidin at concentrations ranging from 100 pg/ml to 10 µg/ml. A linear fit to the data was obtained in the range 1 ng/ml to 100 ng/ml.

FIG. 17 is a series of normalised spectra showing the response of another sensor of the invention for streptavidin to streptavidin concentrations ranging from 100 pg/ml to 10 μg/ml streptavidin. The SPR response for the sensor of FIG. 17 is plotted in FIG. 18.

This shows the SPR response of the sensor saturates at concentrations below 100 pg/ml and at concentrations above 1 μg/ml making the lower detection limit and the higher detection limit in the range of 100 pg/ml and 1 μg/ml respectively for this particular sensor. Hence this sensor would be considered to operate at a range of concentrations between these two limits.

Larger molecules such as proteins may also be attached to silver nanoparticles. The silver nanoparticles of the invention are expected to have an overall negative charge. This charge can play a role in enabling large molecules such as proteins to bind to the silver surface. In the case of proteins a number of features including the net positive charge of a protein (lysine), together with hydrophobic binding (tryptophan) and sulphur bonding (cystine and methinine) can facilitate the attachment between the nanoparticle and protein. This enables proteins to be readily adsorbed onto the nanoparticle surface. Proteins may also be coupled onto the nanoparticles. The use of trisodium citrate in preparing the nanoparticles means that carboxyl groups are present on the nanoparticle surface. This allows the use of well known coupling methods such as carbodiimide coupling to attach proteins to the nanoparticles through a reaction which joins amino groups on the protein to the carboxyl groups on the nanoparticles. The silver nanoparticles in many cases are triangular or hexagonal in shape. These corners present as activated sights for attachment and sensing of proteins.

Figure 19:
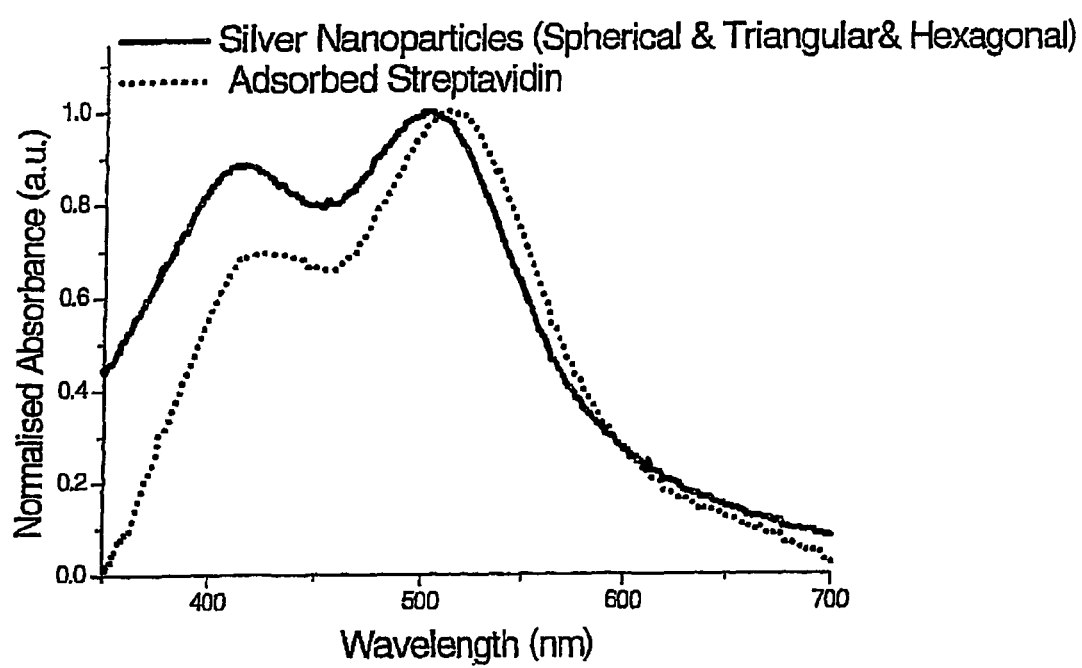
FIG. 19 is a spectrum of a mixture of spherical, triangular and hexagonal silver nanoparticles whose SPR absorption maxima at 417 nm and 502 nm are each shifted to longer wavelengths at 427 and 512 nm respectively in response to streptavidin.
Figure 20:
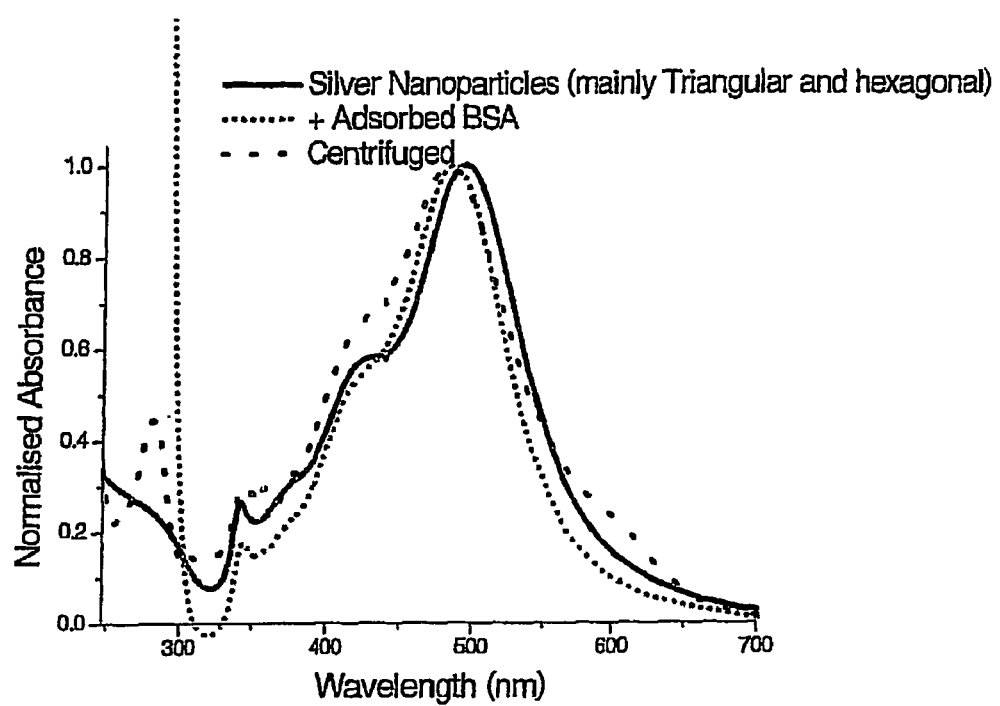
FIG. 20 is a typical spectrum of a mixture of triangular and hexagonal silver nanoparticles whose SPR absorption maximum at 493 nm is shifted to a shorter wavelength at 484 nm in response to BSA at a concentration of 10 mg/ml. The presence of a feature at 280 nm, after centrifugation to remove excess BSA, indicates binding of the BSA to the nanoparticles.

As examples of protein adsorption onto the silver nanoparticle surface two proteins bovine serum albumin (BSA) and Streptavidin are used. The distinctive response of silver nanoparticles to different molecules, in this case proteins, is illustrated herein where streptavidin adsorption is shown to induces a shift of the SPR peak to longer wavelengths as seen in FIG. 19, while BSA induces a shift of the SPR peak to shorted wavelengths as seen in FIG. 20. In the case of the BSA adsorption in FIG. 20 centrifugation was used to remove excess unbound protein. The presence of BSA may be followed by its characteristic absorption peak in the 280 nm region as seen in FIG. 20. It may be noted that the original silver has only a weak feature in this region of the spectrum. On adding the 10 mg/ml BSA solution saturation of the 280 nm feature occurs. After centrifugation, the presence of the attached BSA is indicated by the peak in the 280 nm region.

Figure 21A:
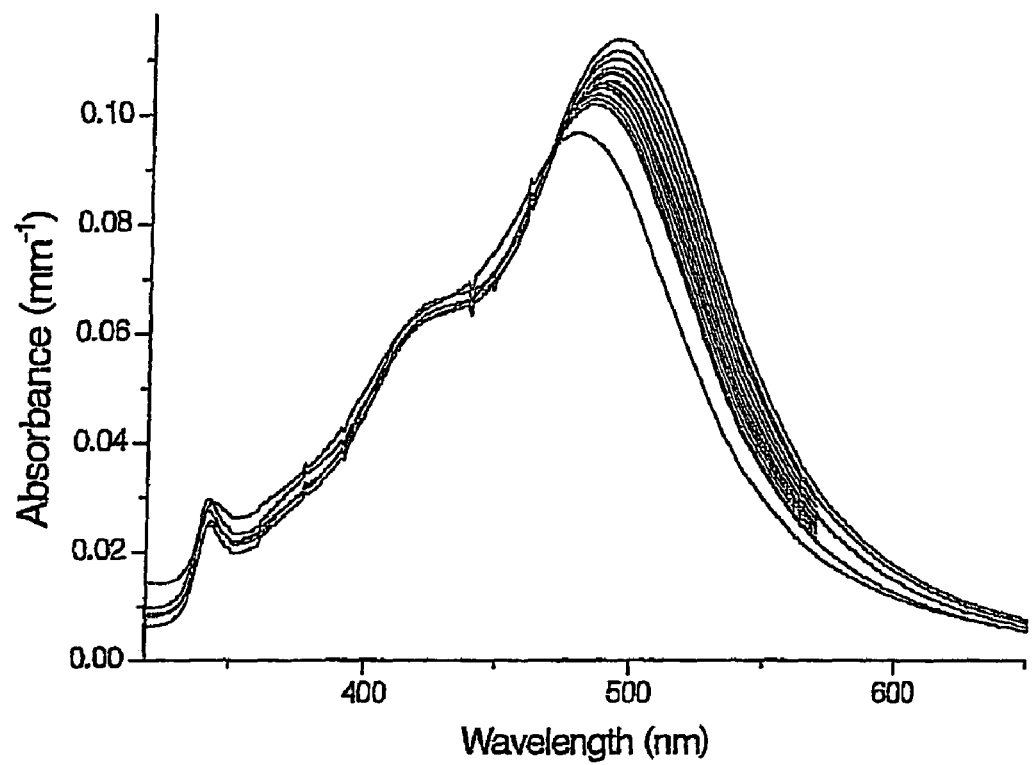
FIG. 21(a) shows the evolution of the SPR spectral shift in response to binding of Bovine Serum Albumin (BSA) onto the nanoparticle surface over time.
Figure 21B:
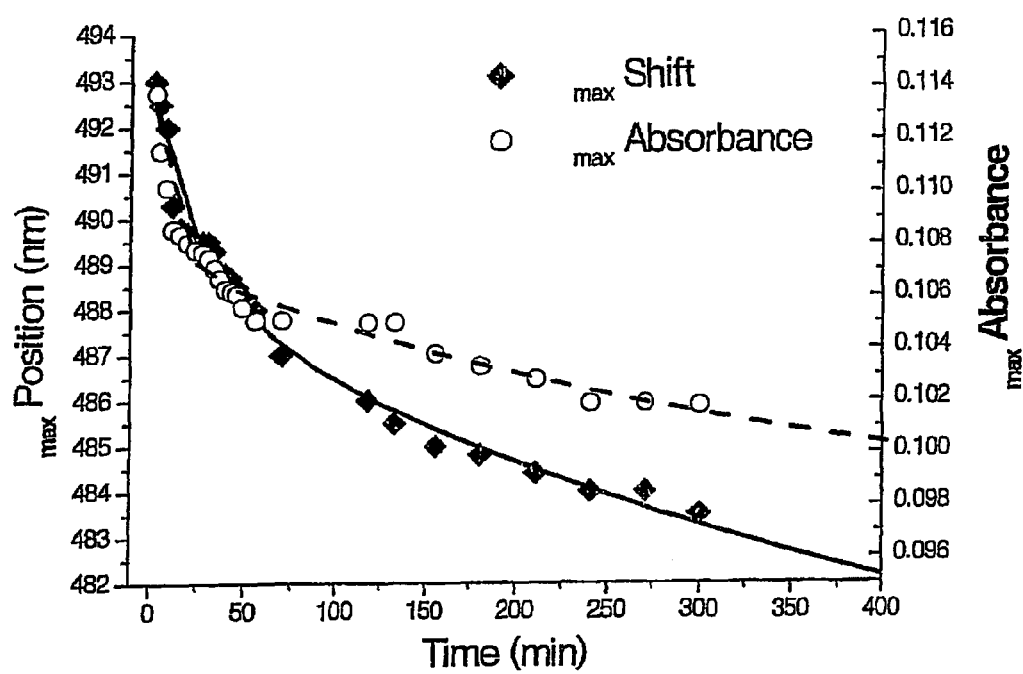
FIG. 21(b) shows a plot of SPR response and the changes in absorption of the nanoparticles of FIG. 21(a) in response to the adsorption of BSA with time.

FIGS. 21(a) and 21(b) show the capacity of the silver nanoparticles to provide information on the rate of a reaction or interaction at their surface. FIG. 21(b) shows the evolution of the SPR spectrum in response to the adsorbance of Bovine Serum Albumin (BSA) onto its surface over time. The SPR of the second peak which corresponds to cornered silver nanoparticles (triangles & hexagons) is originally located at 493 nm and throughout the course of the BSA adsorption the SPR maximum shifts by about 10 nm to 483 nm. A decrease in the absorbance of this peak is also observed where the absorbance changes from 1.14 $mm^{-1}$ to 1.05 $mm^{-1}$ which corresponds to a 7.9% absorbance change. This example also illustrates the increased sensitivity of cornered silver nanoparticles over spherical silver nanoparticles. The spherical nanoparticles whose SPR is located in the 425 nm region show little detectable SPR shift in response to the BSA adsorption. An absorption change of 5.2% is observed for the spherical nanoparticle peak. FIG. 21(b) shows the graph of the cornered nanoparticle SPR shift and absorption change with time.

Figure 22:
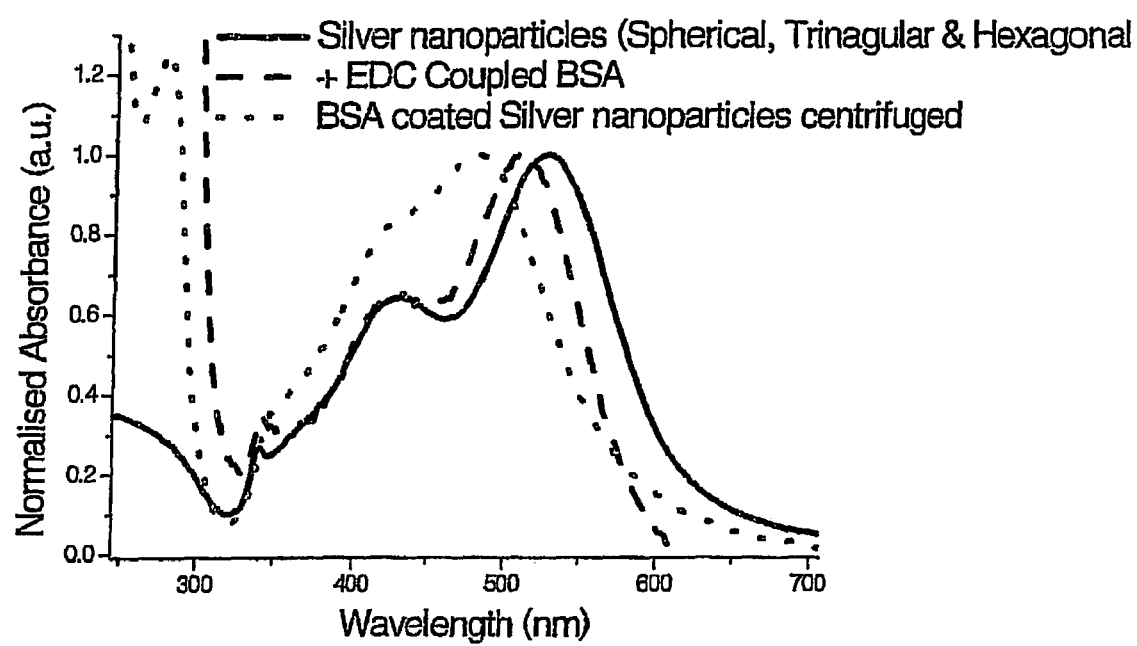
FIG. 22. shows a typical spectrum of a mixture of spherical, triangular and hexagonal silver nanoparticles whose SPR absorption maximum at 527 nm is shifted to 509 nm in response to 10 mg/ml BSA in the presence of 1-ethyl-3-(3-dimethylaminopropyl)-carbodiimide (EDC)

Protein coverage of the nanoparticles may be increased by using a coupling method such as carbodiimide coupling. FIG. 22 shows BSA coated nanoparticles as a result of using N-(3-Dimethylaminopropyl)-N'-ethylcarbodiimide hydrochloride (EDC). Again the 280 nm feature remains strong upon centrifugation indicating the binding to the BSA to the nanoparticle surface.

Figure 23:
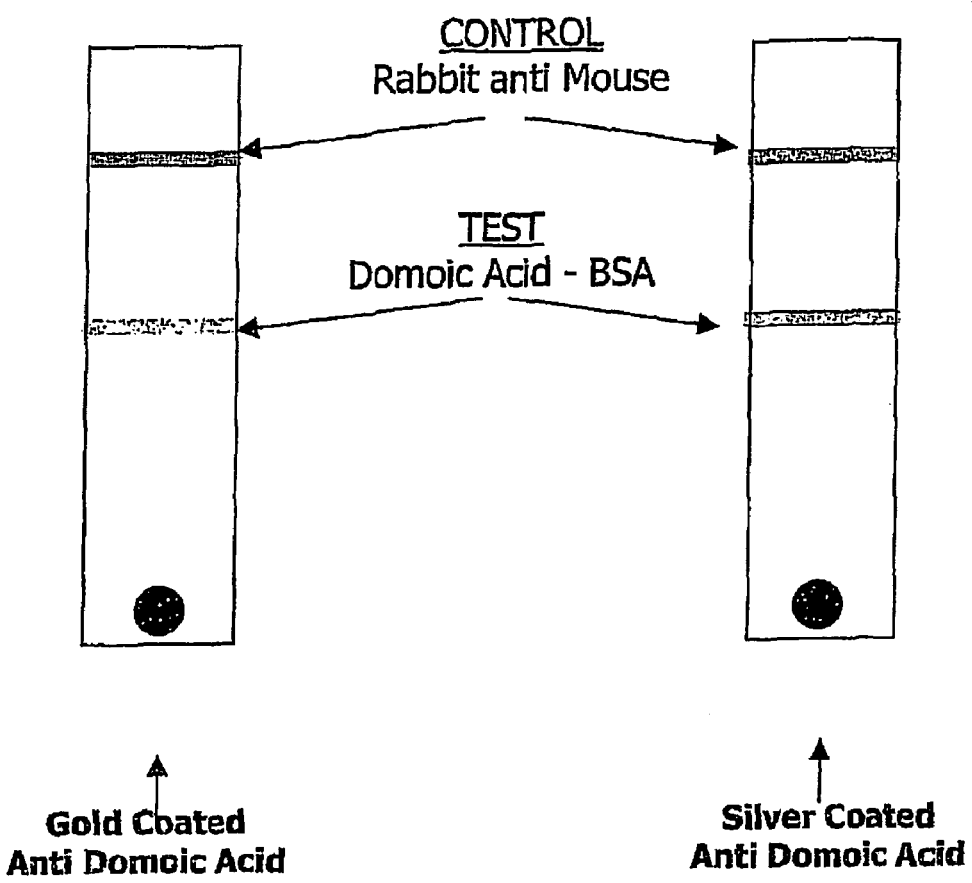
FIG. 23. is a schematic of an embodiment of sensor of the invention in the format of a lateral flow test for domoic acid The performance of the sensor of the invention using silver nanoparticles is compared with using gold nanoparticles as detailed in example 9.

Protein coating of silver nanoparticles may be used to construct sensors akin to ELISA or Lateral flow tests. By coating the silver nanoparticles with antibodies or antigens the antibody/antigen coated silver nanoparticles become a sensor for the corresponding antigen or antibody. As an example a silver nanoparticle sensor for Domoic Acid, which can cause Amnesic Shellfish Poisoning (ASP) in humans, was constructed. Testing for domoic acid is typically carried out using an ELISA test. A lateral flow format was used for the test which demonstrates the usefulness of silver nanoparticles in this type of test format. Gold nanoparticles, which are the typical material used for lateral flow tests, were used as a control test. The test is depicted in FIG. 23. The receptor was domoic-acid antibody (anti-domoic acid), which was adsorbed on to the gold nanoparticle and EDC coupled onto the silver nanoparticles. The lateral flow strip consisted of a control line of rabbit anti-mouse which can bind non-specifically to anti-domoic acid and a test line with domoic acid conjugated to BSA. The silver and gold nanoparticle tests both performed efficiently thus demonstrating the effective application of silver nanoparticles to the lateral flow test format.

Figure 24A:
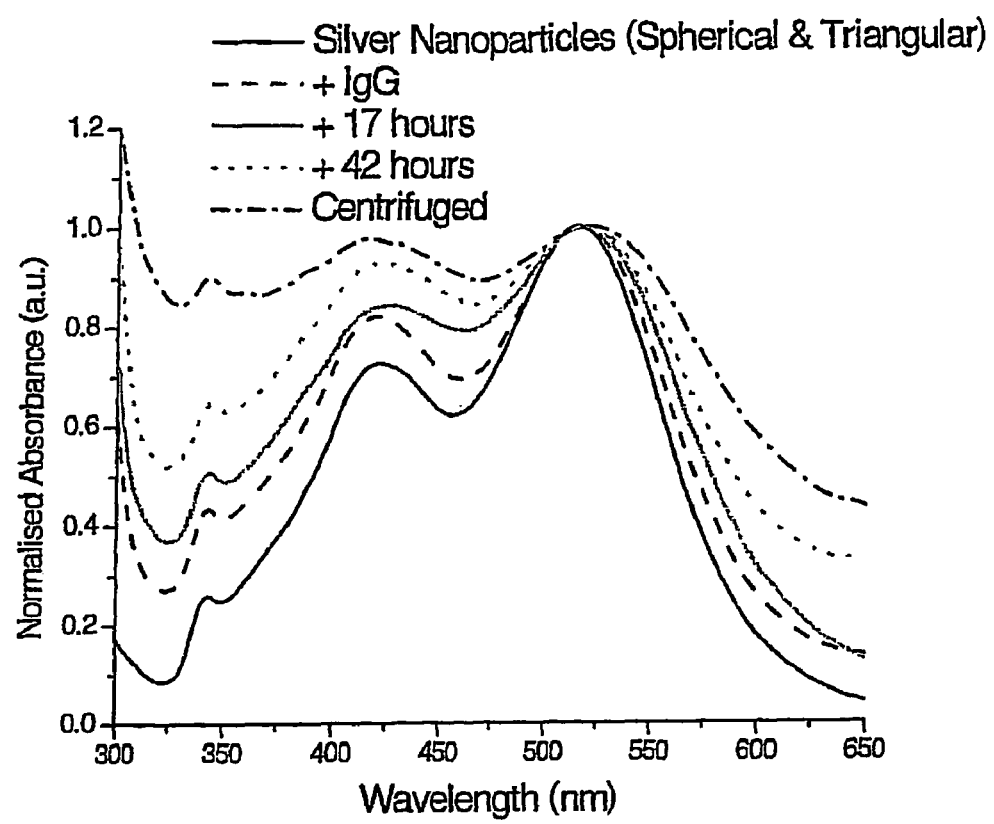
FIG. 24(a) shows a typical series of normalised spectra at various stages in the preparation of a sensor of the invention for the detection of anti-IgG.
Figure 24B:
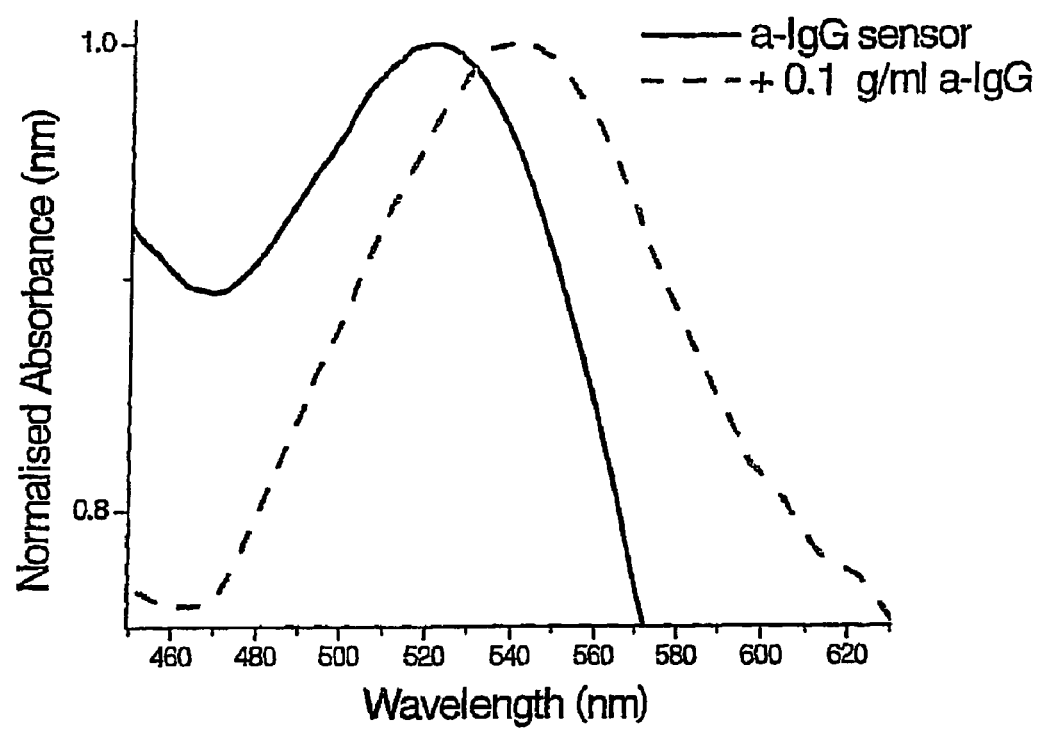
FIG. 24(b) shows the typical response of the sensor of FIG. 24(a) to anti-IgG at a concentration of 0.1 µg/ml. An SPR shift of 21 nm is observed.

The optical format for a sensor of the invention for the antibody, anti-IgG is shown in FIG. 24(b). FIG. 24(a) shows a series of normalised spectra for various stages of the preparation of the anti-IgG sensor. The antigen IgG is used as the receptor. The response of the sensor to 0.1 μg of anti-IgG is shown in FIG. 24(b) where a significant SPR shift of 21 nm is observed. An SPR shift of this magnitude corresponds to a colour change which is readily detectable with the naked eye.

The selectivity of the sensor is achieved through the presence of a receptor which only allows interaction with the desired target analyte(s). In cases where the complete surface area of the silver nanoparticles is not covered by the receptor, a blocking method may be used to prevent possible interference caused by species present in the sample matrix interacting with the exposed silver surface. This blocking method involves binding an un-reactive layer (e.g.: albumin proteins) on to the receptor-coated nanoparticles. This principle is well known in the application of gold nanoparticle technologies.

Figure 25:
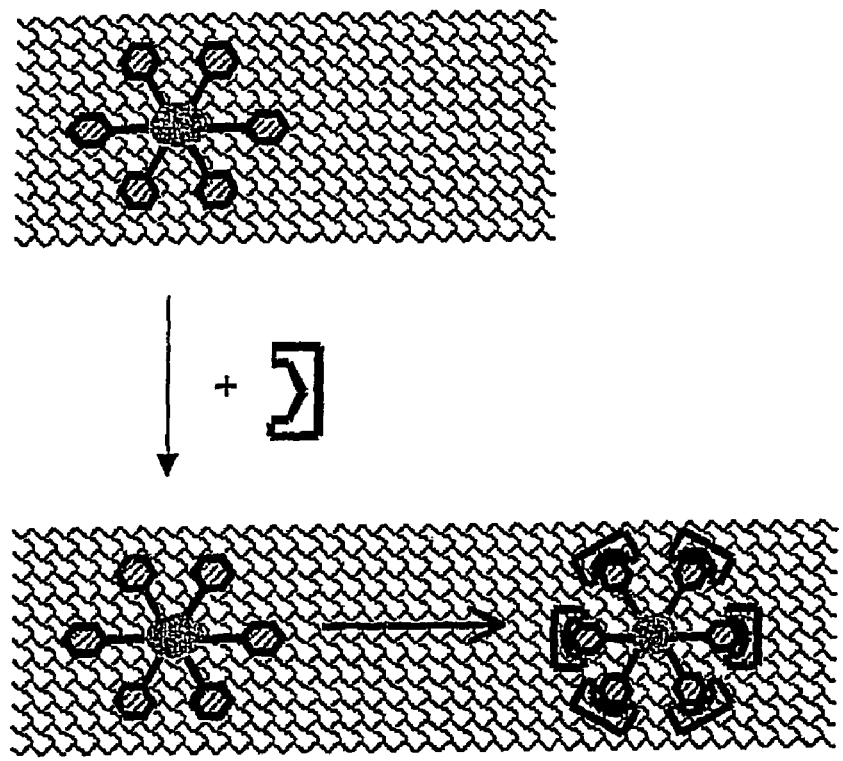
FIG. 25 is a schematic representation of an embodiment of the sensor of the invention whereby the sensor is immobilised on a permeable solid surface.
Figure 25:
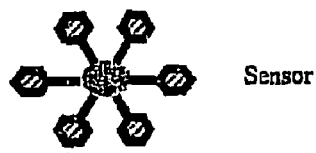
Figure 25:
Figure 25:
Figure 26:
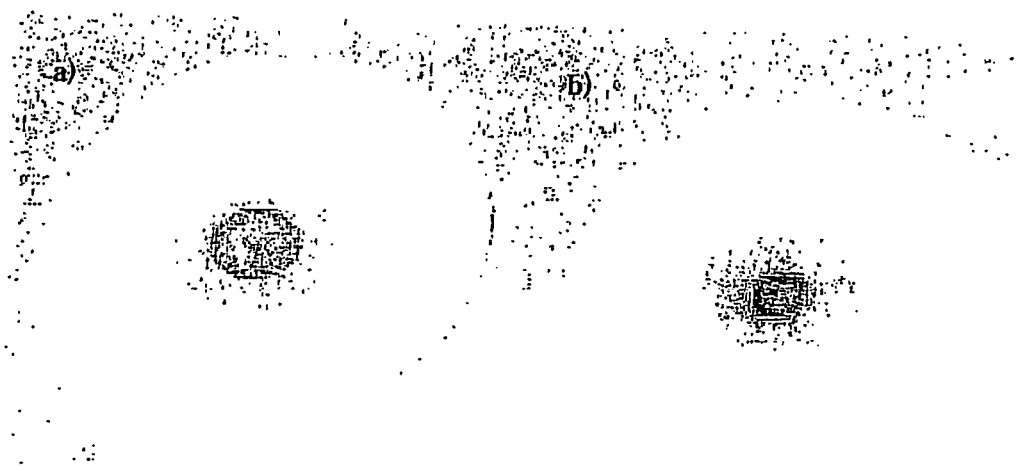
FIG. 26 shows a solid-state silver nanoparticle sensor before (b) and after (a) addition of DMSO.

The sensor may also be used in a solid-state format, as illustrated in FIG. 25. The sensor of the invention was deposited on a nitrocellulose membrane whose pore size was chosen such that dilute solutions of the target analyte passed through the membrane while the sensor's nanoparticles remained trapped in its structure. Upon passing a solution of analyte through the membrane, the analyte interacts with the receptor present on the nanoparticles causing a detectable change in the spectrum.

The sensor of the invention may be cast as a film from polymer solution.

By tailoring the chemical structure of the receptor and linker molecules, it is possible to control the sensitivity of the sensor to its target analyte. Hence, when used qualitatively, the sensor may be tailored to generate a positive response to its target analyte only above a predetermined concentration.

The sensor of the invention is easy to use, even for unskilled operators, and may be developed as a rapid assay suitable for field use. Any suitable means for measuring the change in the absorption spectrum may be used e.g. spectroscopy or colour change visible to the naked eye.

It is envisaged that the sensor of the invention would provide an alternative assay method to replace or complement conventionally used detection methods such as western blotting, direct enzyme assays, radioimmunoassays and enzyme-linked immunosorbent assays (ELISA). The sensor may be designed to detect different target analytes. The sensor may be designed to detect more than one analyte in the same assay.

The sensor may be applied to the detection of biological, chemical and biochemical species in the field of clinical, chemical and environmental analysis.

Figure 27:
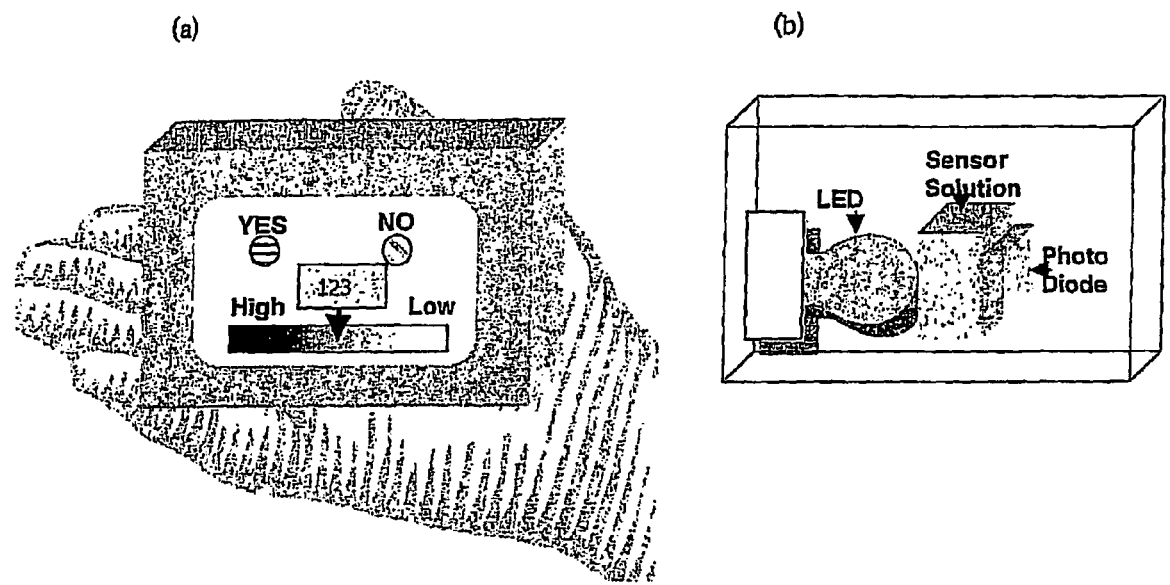
FIG. 27 is a schematic representation of an embodiment of the sensor of the invention in the format of a handheld device. The device as it would appear to the user is depicted in (a), while the components required to construct such a device are illustrated in (b)

The sensor may be manufactured in the form of a hand-held device specific to certain targets of interest in biological, chemical and biochemical analysis. A schematic for such a hand-held device is depicted in FIG. 27. Light-emitting diodes (LEDs) which may have a narrow spectral emission band width, for example, may be used as the light source for the detector. A small volume of sample solution is added to the sensor vessel, or cuvette, within the device. The cuvette may be a single-use component of the device. The instantaneous colour change which occurs in response to detection of the target analyte is measured by the photodiode which may also have a narrow spectral response range. The induced colour change corresponds to a change in the spectra transmission by sensor of the LED emission. The photodiode records the transmission change as a change in its signal voltage.

The device may be calibrated to produce a qualitative or quantitative response to the target analyte. For use as a qualitative device, the signal voltage corresponding to detection of the analyte is used to illuminate a LED on the face of the device which the user observes as a "Yes" response. The device is constructed such that, in the absence of the analyte, a second LED is illuminated which the user observes as a "No" response. For use as a quantitative device, the device is calibrated such that the signal voltage varies in proportion to the concentration of analyte present.

Figure 28:
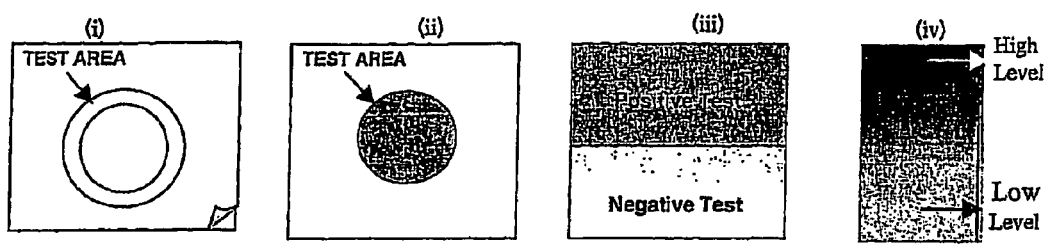
FIG. 28 is a schematic representation of a further embodiment of the sensor of the invention in the format of a rapid assay kit.

A schematic for another such a hand-held device is depicted in FIG. 28. In this case the hand-held device is a single-use kit. A small volume of sample solution is added to the test area containing the sensor which is embedded in a pad. A filtering system maybe used to remove sample material which is not of interest to the test. On removing the filter material the colour change response of the sensor to the detection of the target analyte is observed. The system is calibrated such that a reference card for the colour change corresponding to positive detection of a target analyte is provided for comparison by the user. Similarly the reference colour for the case where detection of the target analyte is absent is also provided.

Portable spectrophotometers are commercially available for field use for chemical and environmental analysis. If detection of various analytes is required, the procedure must be repeated for each analyte of interest. In contrast, the sensor of the invention may incorporate two or more receptors in a single sensor, thereby allowing the operator to test for multiple analytes simultaneously.

The sensor of the invention comprising silver nanoparticles has many other advantages over known detection methods. It provides quantitative and qualitative detection of an analyte. It is highly sensitive. It can give an instantaneous response. The degree of selectivity to the target is controllable. The sensitivity may be controlled to give a positive response above a threshold concentration. The sensor may be used as a multi-target sensor for detecting multiple analytes in a sample. The spectral response of the sensor may take the form of a colour change visible to naked eye. The sensor may be used in solution or the solid state. The sensor may also be used to monitor the rate of a reaction.

The present invention provides a method for producing colloidal particles. More specifically, the invention provides a simple solution phase method for the production of large quantities of silver nanoparticles with defined shapes and consequently, particular optical properties. The control over the linear optical response of nanoparticles enables enhancement of their nonlinear response and has significant potential in optical technologies. The nanoparticles of the invention have great potential for a wide range of applications such as nanoscale sensing, biosensing, imaging and data storage (17-19).

The invention provides a method for controlling nanoparticle morphology and allows the parameters of surface plasmon resonance (SPR) to be effectively tailored. The method provides unprecedented control over the linear optical response of these materials and enables dramatic enhancement of their nonlinear response, giving new momentum to the quest for suitable materials for all optical technologies.

The method of the invention produces silver nanoparticles with multiple plasmon bands, due to the presence of silver particles of non-spherical shape. The method allows for the controlled tuning of the SPR and consequently the systematic colour change of silver nanoparticles. The SPR of the nanoparticles can be tuned so that a wide range of particles of different optical properties can be prepared. The use of PVA as a stabilising agent provides for long term stability and storage of the nanomaterials.

The invention provides for the large scale production of nanoparticles. It can be carried out in solution, it utilises commercially available reagents, it does not require lithographic equipment and the method does not require long reaction times. Synthesis of the nanoparticles may be carried out in an hour.

In the invention silver nanoparticles of average size 20 nm as determined by transmission electron microscopy (TEM), with a variety of morphologies are prepared by a seeding method. The silver nanoparticles obtained by this seeding method exhibit a narrow particle size distribution of ±7 nm. Silver seed nanoparticles are prepared by sodium borohydride reduction of silver ions, in the presence of trisodium citrate. These seed nanoparticles are then added (along with ascorbic acid reducing agent) to a growth solution of silver ions and a polymeric capping agent, with molecular weight greater than 30 kDa, for example, poly(vinyl alcohol) or poly(vinylpyrollidone).

By utilizing the same method of synthesis, including using the same capping material, the same salt, the same temperature and the same solvent, but by changing the ratio of the concentration of the capping material to that of the metal ions, different shapes of silver nanoparticles are produced.

The silver nanoparticles of the invention may show two peaks in their visible absorption spectra. The presence of more than one surface plasmon resonance is believed to be due to the presence of different silver nanoparticle morphologies.

The shape of the nanoparticles is controlled by varying the reaction conditions. By utilising the same method of synthesis, including using the same capping material, the same salt, the same temperature and the same solvent, but by changing the ratio of the concentration of the capping material to that of the metal ions, different shape distributions of silver nanoparticles are produced. The different shapes produced through these variations in the reaction conditions allows the position of the position of second peak in the UV-Visible spectrum to be moved. This results in the preparation of silver nanoparticles of a range of colours, including red, purple and blue. Thus, the colour of the silver nanoparticles may be tuned by altering the conditions used to conduct the seeding method in order to vary their morphology in a controlled manner.

The UV-Visible absorption spectra of the samples were recorded. The absorption data for the samples is summarised below in Table 1:

TABLE 1

| Sample | λ max (nm) | PVA % w/v | Temp. °C. | [Ag+]:[Ag seed ratio] |
|---|---|---|---|---|
| A red | 410,522 | 1 | 40 | 100:1 |
| B purple | 419,542 | 2.5 | 40 | 50:1 |
| C blue | 410,578 | 5 | 40 | 50:1 |
| D yellow | 439 | 5 | 4 | 50:1 |
| E red | 502 | 1 | 22 | 100:1 |

The results show that the method provides a simple but effective method of controlling the colour of silver nanoparticles by variation of the position of the second plasmon band.

Figure 5:
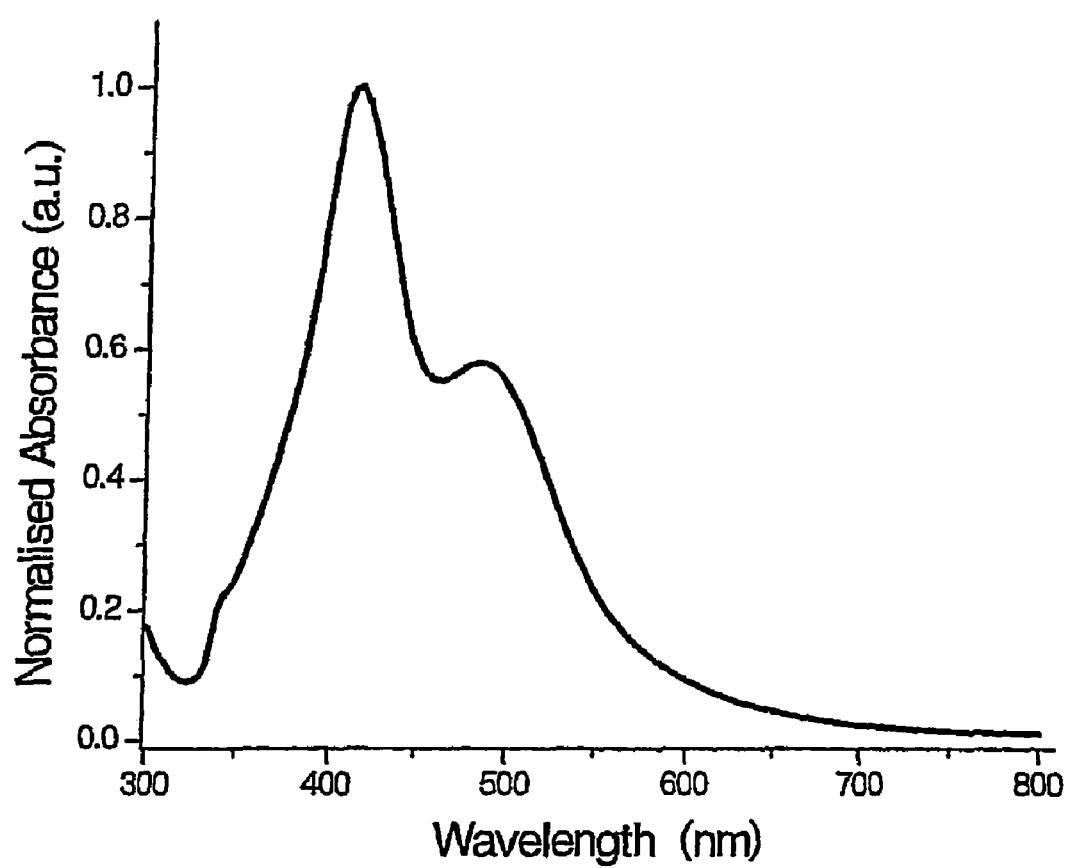
FIG. 5 shows a typical spectrum of a mixture of silver nanoparticles containing spherical, triangular and hexagonal morphologies which were produced in darkness.

FIG. 4 shows the electronic absorption spectra of samples A, B, C and D. FIG. 5 shows the electronic absorption:spectrum of sample E.

The size and shape of the nanoparticles was determined by transmission electron microscopy. The size of the nanoparticles samples A-E as determined from TEM images were:
A: 20±8 nm
B: 22±8 nm
C: 19±4.5 nm
D: 31±9 nm
E: 56±7 nm The results show that these particles are significantly smaller than non-spherical particles produced by other methods. Consequently, these particles are expected to show improved long term stability as compared with the larger particles prepared by other synthetic methods.

The predominant particle shape associated with each sample is shown in FIG. 4(b). For example, for sample A, the predominant particle shape is triangular—55% of particles sampled show this morphology. Other particle shapes i.e. spheres, hexagons and rods are observed in smaller amounts, (22%, 14% and 9% respectively).

The predominant nanoparticle morphology was found to be highly dependent on the reaction conditions used, particularly PVA concentration. The presence of elemental silver was confirmed by Energy Dispersive X-ray analysis.

The nanoparticles that are produced by this method may have use in a number of applications as follows:

1. Surface enhanced raman scattering (SERS) is an analytical technique used for the detection of very low concentrations of molecules. The high sensitivity of this technique is due to the enhanced Raman scattering exhibited by molecules that are adsorbed onto particular surfaces. The silver nanoparticles that are produced by the method of the invention can be used as the surfaces (substrates) onto which the analytes are adsorbed. This is because the nanoparticles absorb strongly at the excitation wavelength, 514 nm, which is used in this technique.
2. The strong absorption of the nanoparticles at this wavelength shows enhanced optical nonlinearity. Materials with such enhanced, ultrafast nonlinear optical response are required for the development of photonic devices.
3. The position of the surface plasmon resonance (i.e. the wavelength at which it occurs) is sensitive to changes in the local environment of the nanoparticles. Therefore, changes in the plasmon band can be used to detect binding of other molecules to the nanoparticles and provide a method of biosensing.
4. The nanoparticles may be used in catalysis since they have large surface-volume ratios and the generation of different nanoparticle morphologies would allow tailoring of the catalyst for different reactions.

Carrying out the reaction under controlled irradiation conditions allows the generation of mixtures of nanoparticles having only hexagonal and triangular morphologies. Such samples show a single absorption peak between 470 and 600 nm.

FIGS. 1a and 1b relate to spherical nanoparticles only. FIGS. 2(a), 2(b) and 5 relate to a mixture of spherical, triangular and hexagonal nanoparticles. A mixture of spherical and cornered nanoparticles is useful since the cornered nanoparticles are more sensitive to changes in their environment than spherical ones because significantly higher amplitude SPR has been shown (20) to occur at corners on nanoparticles. The sharper the corner on the nanoparticle, the greater the increase in amplitude of the SPR. The ratio of the changes induced in SPR peaks of the two types of nanoparticles can provide important information for sensing.

FIGS. 3(a) and 3(b) relate to cornered nanoparticles e.g. a mixture of triangular and hexagonal nanoparticles only. The absence of an absorption peak in the 410 nm region indicates the absence of spherical nanoparticles. These cornered nanoparticles are especially advantageous due to their very high sensitivity.

FIGS. 8 and 9 demonstrate the enhanced sensitivity of silver nanoparticles over gold nanoparticles. The silver nanoparticles exhibit an 11 nm shift to the solvent dimethyl sulfoxide (DMSO) whereas a shift of only 0.5 nm is found in the case of gold.

The silver nanoparticle-based sensor of the invention may be modified to detect any analyte of interest provided that a suitable receptor is prepared and adsorbed onto the available surface of the silver nanoparticles. It is envisaged that sensors having nanoparticles bearing, for example, biotin or carboxylic acid groups suitable for subsequent functionalisation may also be prepared. The end-user may then functionalise the sensor with an appropriate receptor to conduct a range of assays as required.

The invention will be more clearly understood from the following examples.

Example 1

Preparation of Silver Seeds

A 20 ml solution with final concentration of $2.5 \times 10^{-4}$ M $AgNO_3$ and $2.5 \times 10^{-4}$ M trisodium citrate in water was prepared. $NaBH_4$ (0.01 M, 0.6 ml) was added with vigorous stirring. A colour change from colourless to yellow was observed, indicating formation of silver seed nanoparticles.

Example 2(i)

Preparation of Silver Nanoparticles

Poly(vinyl alcohol) (PVA)-silver nanoparticles were typically prepared as follows: aqueous $AgNO_3$ (0.01 M, 0.25 ml) was added to aqueous PVA of molecular weight (mol. wt.) 89 kD-98 kD (10 ml, 1% w/v). Silver seeds ($2.5 \times 10^{-4}$ M, 0.1 ml) and ascorbic acid (0.1 M, 0.05 ml) were then added simultaneously with stirring.

Example A

Preparation of Red Silver Nanoparticles

Aqueous PVA (mol. wt. 89 kD-98 kD, 1% w/v, 10 ml) and aqueous AgNO$_3$ (0.01 M, 0.25 ml) were added to a reaction vessel. The mixture was heated to 40° C. Silver seed nanoparticles prepared according to example 1 (0.1 ml) and ascorbic acid (0.1 M, 0.05 ml) were added simultaneously—a colour change from colourless to red was observed. The silver nanoparticles were incubated at 40° C. for one hour, then transferred to a sample tube and stored in the dark at 4° C.

Example B

Preparation of Purple Silver Nanoparticles

Aqueous PVA (mol. wt. 89 kD-98 kD, 2.5% w/v, 10 ml) and aqueous AgNO$_3$ (0.01 M, 0.25 ml) were added to a reaction vessel. The mixture was heated to 40° C. Silver seed nanoparticles prepared according to example 1 (0.2 ml) and ascorbic acid (0.1 M, 0.05 ml) were added simultaneously—a colour change from colourless to purple was observed. The silver nanoparticles were incubated at 40° C. for one hour, then transferred to a sample tube and stored in the dark at 4° C.

Example C

Preparation of Blue Silver Nanoparticles

Aqueous PVA (mol. wt. 89 kD-98 kD, 5% w/v, 10 ml) and aqueous AgNO$_3$ (0.01 M, 0.25 ml) were added to a reaction vessel. The mixture was heated to 40° C. Silver seed nanoparticles prepared according to example 1 (0.2 ml) and ascorbic acid (0.1 M, 0.05 ml) were added simultaneously—a colour change from colourless to blue was observed. The silver nanoparticles were incubated at 40° C. for one hour, then transferred to a sample tube and stored in the dark at 4° C.

Example D

Preparation of Yellow Silver Nanoparticles

Aqueous PVA (mol. wt. 89 kD-98 kD, 5% w/v, 10 ml) and aqueous AgNO$_3$ (0.01 M, 0.25 ml) were added to a reaction vessel. The mixture was cooled to 4° C. in an ice-water bath. Silver seed nanoparticles prepared according to example 1 (0.2 ml) and ascorbic acid (0.1 M, 0.05 ml) were added simultaneously—a colour change from colourless to yellow was observed. The silver nanoparticles were incubated at 4° C., then transferred to a sample tube and stored in the dark at 4° C.

Example E

Preparation of Red Silver Nanoparticles by Irradiation

Aqueous PVA (mol. wt. 89 kD-98 kD, 1% w/v, 10 ml) and aqueous AgNO$_3$ (0.01 M, 0.25 ml) were added to a reaction vessel. Silver seed nanoparticles prepared according to example 1 (0.1 ml) were added to the mixture. The reaction vessel was placed at a distance of 60 cm from a xenon lamp (Oriel Xe, luminance 12 cd/m$^2$). Ascorbic acid (0.1 M, 0.05 ml) was added and the reaction vessel was shaken to ensure mixing. A colour change from colourless to red was observed after about 30 seconds. The silver nanoparticles were incubated, then transferred to a sample tube and stored in the dark at 4° C.

Example F

Preparation of Silver Nanoparticles in the Dark

Silver nanoparticles were prepared following the method described in example A except that the procedure was conducted in a darkroom. The absorption spectrum of this sample is shown in FIG. 5.

Example 2(ii)

Preparation of Silver Nanoparticles Using PVP as Stabilizing Agent

Silver nanoparticles were prepared at 40° C. according to the method described in example 2(i)B, but using 2.5% (w/v) PVP as stabilizer. Using PVP of molecular weight 10 kD yielded nanoparticles having a single absorption peak at 410 nm; using PVP of molecular weight 55 kD yielded nanoparticles having absorption peaks at 410 nn and 544 nm.

Example 3(i)

Response of Silver Nanoparticle Sensor to DMSO

To 0.4 ml of silver nanoparticle solution prepared according to example 2 was added 0.1 ml DMSO. A response of the silver nanoparticle sensor to DMSO was observed whereby the absorption peak in the spectrum shifted by 11 nm.

Example 3(ii)

Response of Sun et al's Silver Nanoparticles to DMSO

To 0.4 ml of silver nanoparticle solution prepared according to the procedure described by Sun et al (16) was added 0.1 ml DMSO. A response of the silver nanoparticle sensor to DMSO was observed whereby the absorption peak in the spectrum shifted by 6 nm.

Example 4

Deposition of a Biotin Layer on Silver Nanoparticles in Two Stages

A solution of silver nanoparticle produced according to example 2 (having a silver content of 2.5×10$^{-4}$ M in water) and was incubated with a mixture of alkanethiol and mercapto-acid having a total concentration of 1 mM in ethanol at room temperature overnight, allowing an alkanethio/mercapto-acid layer, most probably a monolayer, to form on the surface of the silver nanoparticles. The resulting silver nanoparticles bearing an alkanethiol/mercapto-acid layer were recovered by centrifuging. After resuspension in water or aqueous buffer, (+)-biotinyl-3,6-dioxaoctanediamine, (EZ-Link™ Biotin-PEO-amine, Pierce Biotechnology) was added to the alkanethiol/mercapto-acid-coated silver nanoparticles in the presence of 1-ethyl-3-(3-dimethylaminopropyl)carbodiimide hydrochloride (EDC, Pierce Biotechnology) at a ratio of 1 mM biotin-PEO-amine: 1 mM EDC. The resulting product was recovered by centrifuging and resuspended in water or aqueous buffer. The biotinylated nanoparticles thus obtained bears receptors capable of binding selectively to analytes of interest, e.g.: streptavidin, anti-biotin etc.

Example 5

Deposition of a Biotinylated Layer on Silver Nanoparticles in One Stage

Sulfosuccinimidyl-6'-(biotinamido)-6-hexanamido hexanoate (Sulfo-NHS-LC-LC-biotin, Pierce Biotechnology) was reacted with an aminoalkanethiol yielding a thiol-terminated biotin derivative. Silver nanoparticles produced according to example 2 were incubated with the biotin derivative in an aqueous buffer e.g.: 0.1 M MES(2-(N-Morpholino) ethansulfonic acid) at room temperature overnight, allowing a biotinylated layer, most probably a monolayer to form on the surface of the silver nanoparticles. The resulting product was recovered by centrifuging and resuspended in water or aqueous buffer. The biotinylated nanoparticles thus obtained bear receptors capable of binding selectively to analytes of interest, e.g.: streptavidin, anti-biotin.

Example 6

Alternative Direct Method for the Biotinylation of Ag Nanoparticles

A biotinylating solution was prepared by adding 1 mM (+)-Biotinyl-3,6-dioxaoctanediamine to an equal volume of 1 mg/ml 1-ethyl-3-(3-dimethylaminopropyl)carbodiimide hydrochloride (EDC) in an aqueous buffer e.g.: 0.1 M MES (2-(N-Morpholino)ethansulfonic acid), pH 5.5. A known volume of a solution of nanoparticles produced according to example 2 ($2.5 \times 10^{-4}$ M silver content, in water) was centrifuged and the supernatant removed. An equal volume of biotinylating solution was added to the silver nanoparticles and the pellet was resuspended through shaking or use of a vortex. The suspension was is stirred gently and allowed incubate for up to 48 hours at room temperature. The resulting biotinylated silver nanoparticles were recovered by centrifuging and resuspended in water or aqueous buffer.

Example 7(i)

Deposition of Bovine Serum Albumin onto Silver Nanoparticles 0.5 ml of a solution of Bovine Serum Albumin (BSA) in water or aqueous buffer (e.g. 0.1 M MES, pH 5.5), preferably having a concentration ranging from 1 µg/ml to 10 mg/ml, was added to an equal volume of a solution of silver nanoparticles produced according to example 2. The mixture was stirred gently and incubated at room temperature for between one and 24 hours. After incubation, the BSA-coated silver nanoparticles were recovered by centrifuging and resuspended in water or aqueous buffer.

Example 7(ii)

Coupling Bovine Serum Albumin onto Silver Nanoparticles 0.2 ml of 10 mg/ml Bovine Serum Albumin (BSA) in aqueous buffer (e.g.: 0.1 M MES, pH 5.5) was added to an equal volume of 1 mg/l EDC hydrochloride in the same buffer. This solution was added to 0.2 ml of a solution of silver, nanoparticles produced according to example 2 and incubated for between 2 and 24 hours at room temperature. After incubation, the BSA-coated silver nanoparticles were recovered by centrifuging and resuspended in water or aqueous buffer.

Example 8(i)

Deposition of Streptavidin onto Silver Nanoparticles 0.5 ml of a solution of streptavidin in water or aqueous buffer (e.g. 0.1 M MES, pH 5.5), preferably having a concentration ranging from 10 µg/ml to 10 mg/ml, was added to an equal volume of a solution of silver nanoparticles produced according to example 2. The mixture was stirred gently and incubated at room temperature for between one and 24 hours. After incubation, the streptavidin-coated silver nanoparticles were recovered by centrifuging and resuspended in water or aqueous buffer.

Example 8(ii)

Coupling Streptavidin onto Silver Nanoparticles 0.2 ml of 10 mg/ml streptavidin in aqueous buffer (e.g.: 0.1 M MES, pH 5.5) was added to an equal volume of 1 mg/ml EDC hydrochloride in the same buffer. This solution was added to 0.2 ml of a solution of silver nanoparticles produced according to example 2 and incubated for between 2 and 24 hours at room temperature. After incubation, the streptavidin-coated silver nanoparticles were recovered by centrifuging and resuspended in water or aqueous buffer.

Example 9

Detection of Streptavidin in Solution

Biotinylated silver nanoparticles were prepared as described in examples 4-6 using solutions of biotin at concentrations ranging from 1 mM to 1 nM, more preferably 0.1 mM to 0.01 mM. Streptavidin was added to each sample at concentrations ranging from 1 mg/ml to 100 pg/ml. In all cases, detection of streptavidin was observed as a shift of, the SPR spectral peaks accompanied by a change in the ratio of the relative intensity of the SPR bands for nanoparticles having more than one SPR peak. No further shift was apparent in the spectrum after 24 hours.

Example 10

Detection of Streptavidin in the Solid State

Biotinylated nanoparticles, prepared as described in examples 4-6, but using a higher concentration of silver, were deposited on a nitrocellulose membrane whose pore size was chosen such that dilute solutions of the analyte of interest could pass through the membrane while the biotinylated nanoparticles remain trapped in its structure. Successive additions of biotinylated nanoparticles may be made to the membrane to obtain an intensely coloured region.

A solution of streptavidin was passed through the membrane. The streptavidin bound to the biotin present on the nanoparticles causing a loss of intensity in their spectrum. A positive test result was indicated by observing a loss of colour on the membrane. The test may be modified to detect any analyte of interest where a suitable receptor is adsorbed onto the available surface of the silver nanoparticles in the manner described in the examples above.

Example 11

Domoic Acid Lateral Flow Test Using Silver Nanoparticles 0.5 ml of a solution of silver nanoparticles prepared according to example 2 were centrifuged and the supernatant removed. 5 mg/ml EDC and 0.5 mg/ml domoic acid in aqueous buffer, e.g.: PBS was added to the silver nanoparticle pellet and the whole was resuspended using a vortex. The suspension was stirred gently and incubated at room temperature for 3 hours. 25 µl of 10% w/v human serum albumin (HSA) was added and the whole stirred for another 10 minutes. The suspension was centrifuged, the supernatant removed and the pellet resuspended in PBS. 34 drops of the resuspended silver nanoparticles were added to lateral flow strips having rabbit anti-mouse as the control line and domoic acid conjugated to BSA as the test line. The lateral flow strip were stood in a 0.5 M solution of surfactant, e.g: Tween. After allowing the solution to rise to the top of the lateral flow strip, the strip was removed from the solution and examined for the presence of control and test lines.

Example 12

Preparation of An Anti-IgG Sensor And Detection of Anti-IgG 0.5 ml aliquots of a solution of silver nanoparticles prepared according to example 2 were centrifuged and the supernatant removed. 1 mg/ml EDC was added to an equal volume of IgG, preferably having a concentration ranging from 10 µg/ml to 10 mg/ml in aqueous buffer (e.g.: 0.1 M MES, pH 5.5). 0.5 ml of this solution was added to each aliquot of nanoparticles produced according to example 2 and incubated for between 2 and 36 hours at room temperature. After incubation, the IgG coated silver nanoparticles were recovered by centrifuging and re-suspended in water or aqueous buffer. Anti-IgG was added to each aliquot at concentrations ranging from 1 mg/ml to 100 pg/ml. In all cases, detection of streptavidin was observed as a shift of, the SPR spectral peaks accompanied by a change in the ratio of the relative intensity of the SPR bands for nanoparticles having more than one SPR peak. No further shift was apparent in the spectrum after 24 hours.

Example 13

Handheld Device

A device was constructed as illustrated in FIG. 27 consisting of a LED, sample cuvette, photodiode detector and voltmeter. A LED having 100 nm spectral width and peak emission at 490 nm was used. 0.4 ml of a solution of silver nanoparticles prepared according to example 2 was added to the sample cuvette, placed in the optical path of the LED and the voltage output from the photodiode recorded. 0.1 ml DMSO was added to the sample cuvette and the voltage output from the photodiode recorded again. A change in voltage of 20 mV was observed in response to the presence of DMSO.

The handheld device may produce a quantitative response to the presence of a target analyte whereby an observed change in voltage indicates the presence of the analyte, or it may produce a qualitative response whereby the change in voltage observed is proportional to the concentration of analyte present.

Example 14

Colourimetric Rapid Assay Kit

A silver nanoparticle sensor of the invention may be deposited on a porous membrane, for example nitrocellulose, whose pore size was chosen such that dilute solutions of the analyte of interest could pass through the membrane while the biotinylated nanoparticles remain trapped in its structure. Successive additions of nanoparticles may be made to the membrane to obtain an intensely coloured region.

A solution of the sample matrix is passed through the membrane. If the target analyte is present in the matrix, it may bind to the sensor, causing a detectable change in their spectrum. Most preferably, this detectable change is a colour change visible to the naked eye.

The assay kit may produce a quantitative response to the presence of a target analyte whereby an observed colour change indicates the presence of the analyte, or it may produce a qualitative response whereby the extent of the colour change observed is proportional to the concentration of analyte present.

The invention is not limited to the embodiments hereinbefore described which may be varied in detail.

REFERENCES

1. Park S. J et al, "Array-based electrical detection of DNA with nanoparticle probes", Science vol. 295 pp. 1503-1506 (2002).
2. Taton T. A et al, "Two-color labelling of oligonucleotide arrays via size-selective scattering of nanoparticle probes", J. Am. Chem. Soc. vol 123 pp. 5164-5165 (2001)
3. Reynolds R. A. et al., "Homogeneous, Nanoparticle-Based Quantitative Colorimetric Detection of Oligonucleotides" J. Am. Chem. Soc., vol. 122, pp. 3795-3796 (2000)
4. WO0151665
5. Link S. et al., "Spectral Properties and Relaxation Dynamics of Surface Plasmon Electronic Oscillations in Gold and Silver Nanodots and Nanorods", Phys. Chem. B, vol. 103, pp. 8410-8426 (1999).
6. Mock J. J. et al., "Shape effects in plasmon resonance of individual colloidal silver nanoparticles" J. Chem. Phys, vol. 116, pp. 6755-6759 (2002).
7. Jin R. et al., "Photoinduced Conversion of Silver Nanoplates to Nanoprisms, Science, vol. 294, pp. 1901-1903. (2001).
8. Chen S. et al., "Synthesis and Characterization of Truncated Triangular Silver Nanoplates", Nano Letters, vol. 2, pp. 1003-1007 (2002).
9. Zhou Y. et al., "A Novel Ultraviolet Irradiation Photoreduction Technique for the Preparation of Single-Crystal Ag Nanorods and Ag Dendrites", Adv. Mater, vol. 10, pp. 850-852 (1999).
10. Jana R. et al., "Wet chemical synthesis of silver nanorods and nanowires of controllable aspect ratio", Chem. Comm., pp. 617-618 (2001)
11. Haynes C. L et al., "Nanosphere Lithography: A Versatile Nanofabrication Tool for Studies of Size-Dependent Nanoparticle Optics", J. Phys. Chem. B, vol. 105, pp. 5599-5611 (2001)
12. Haes, A. J. et al., "A nanoscale optical biosensor: sensitivity and selectivity of an approach based on the localised surface plasmon resonance spectroscopy of triangular silver nanoparticles", *J. Am. Chem. Soc.*, vol. 124, pp. 10596-10604 (2002).
13. Jensen, T. R. et al., "Nanosphere lithography: tunable localised surface plasmon resonance spectra of silver nanoparticles", *J. Phys. Chem. B*, vol. 104 pp. 10549-10556 (2000).
14. Malinsky, M. D. et al., "Chain length dependence and sensing capabilities of the localised surface plasmon resonance of silver nanoparticles chemically modified with alkanethiol self-assembled monolayers", *J. Am. Chem. Soc.*, vol. 123 1471-1482 (2001).
15. Riboh, J. C. et al., "A nanoscale optical biosensor: real time immunoassay in physiological buffer enabled by improved nanoparticle adhesion", *J. Phys. Chem. B*, vol. 107 pp. 1772-1780 (2003).
16. Sun Y. et al, "Transformation of silver nanospheres into nanobelts and triangular nanoplates through a thermal process", *Nano Lett.*, vol. 3, pp. 675-679 (2003).
17. Bonnemann H. et al., "Nanoscopic Metal Particles—Synthetic Methods and Potential Applications", *Eur. J. Inorg. Chem.*, pp. 2455-2480 (2001).
18. Shipway A. N, et al., "Nanoparticles as structural and functional units in surface-confined architectures", *Chem. Comm.*, pp. 2035-2045 (2001)
19. Trinidade T. et al., "Nanocrystaline Semiconductors: Synthesis, Properties, and Prespectives", *Chem. Mater.*, vol. 13, pp. 8343-3858 (2001)
20. Kottmann J. P. et al., "Field polarization and polarization charge distributions in plasmon resonant nanoparticles", *New Journal of Physics* vol. 2 pp. 1-27 (2000).

The invention claimed is:

1. A sensor for biosensing comprising discrete silver nanoparticles that are shaped and substantially plate-like in structure dispersed in an aqueous based system in which substantially all of the surfaces of the silver nanoparticles are available for interaction with an analyte or for functionalisation with a receptor which is capable of interacting with an analyte, wherein the silver nanoparticles provide a detectable change of from 1 to 150 nm in the position of their surface plasmon resonance in the UV-visible absorption spectrum in response to the binding of an analyte.

2. The sensor as claimed in claim 1 wherein a receptor specific to a target analyte is attached to the surface of the nanoparticles.

3. The sensor as claimed in claim 2 wherein the receptor is bonded directly to the surface of the nanoparticles.

4. The sensor as claimed in claim 2 wherein a linker is provided between the receptor and the silver nanoparticles.

5. The sensor as claimed in claim 4 wherein the linker incorporates an organic or an inorganic functional group.

6. The sensor as claimed in claim 5 wherein the functional group comprises a thiol group or an amine group.

7. The sensor as claimed in claim 1 wherein more than one type of receptor is attached to the silver nanoparticles.

8. The sensor as claimed in claim 1 wherein the silver nanoparticles have dimensions in the range of from 5 to 100 nm.

9. The sensor as claimed in claim 1 wherein the silver nanoparticles have dimensions in the range of from 18 nm to 32 nm.

10. The sensor as claimed in claim 1 wherein the morphology of at least some of the silver nanoparticles is hexagonal and/or triangular in shape.

11. The sensor as claimed in claim 1 wherein at least some of the silver nanoparticles display an SPR peak in the 400 nm region.

12. The sensor as claimed in claim 1 wherein at least some of the silver nanoparticles display an SPR peak in the 470 to 600 nm region.

13. The sensor as claimed in claim 1 wherein at least some of the silver nanoparticles display an SPR peak in the 340 nm region.

14. The sensor as claimed in claim 1 wherein the silver nanoparticles show predominantly non-spherical morphology.

15. A method for detecting an analyte comprising contacting the analyte with a sensor as claimed in claim 1 and observing a detectable change.

16. The method as claimed in claim 15 wherein the detectable change is a change in the absorption spectrum.

17. The method as claimed in claim 15 wherein the detectable change is a qualitative or quantitative change.

18. The method as claimed in claim 15 wherein the change is a colour change observable with the naked eye.

19. The method as claimed in claim 18 wherein the change in the absorption spectrum is a shift which is detected in the range from 200 nm to 900 nm.

20. The method as claimed in claim 19 wherein the shift is from 1 to 150 nm.

21. The method as claimed in claim 19 wherein the shift is from 5 to 50 nm.

22. A method for preparing silver nanoparticles which comprises the step of forming the nanoparticles in the presence of a polymeric stabiliser.

23. The method as claimed in claim 22 comprising the step of controlling the optical response of the silver nanoparticles by varying the concentration of the polymeric stabiliser.

24. The method as claimed in claim 22 wherein the polymeric stabiliser has a molecular weight of greater than 10 kDa.

25. The method as claimed in claim 24 wherein the molecular weight of the polymeric stabiliser is less than 1300 kDa.

26. The method as claimed in claim 22 wherein the polymeric stabiliser is water soluble.

27. The method as claimed in claim 22 wherein the polymeric stabiliser is selected from one or more of poly(vinyl alcohol), poly(vinylpyrollidone), poly(ethylene glycol), and poly(acrylic acid).

28. The method as claimed in claim 22 wherein the polymeric stabiliser is poly(vinyl alcohol).

29. The method as claimed in claim 22 wherein the method comprises reducing a silver salt.

30. The method as claimed in claim 29 wherein the silver salt is silver nitrate.

31. The method as claimed in claim 22 wherein the reaction is carried out in the presence of seed silver nanoparticles.

32. The method as claimed in claim 30 wherein the reaction is carried out in the presence of seed silver nanoparticles.

33. The method as claimed in claim 32 wherein the ratio of [silver nitrate] to [silver seed] is greater than or equal to 50:1.

34. The method as claimed in claim 32 wherein the ratio of [silver nitrate] to [silver seed] is between 50:1 and 200:1.

35. The method as claimed in claim 32 wherein the ratio of [silver nitrate] to [silver seed] is between 50:1 and 100:1.

36. The method as claimed in claim 22 wherein the reaction is carried out in an aqueous medium.

37. The method as claimed in claim 29 wherein the reduction is carried out at a temperature of from 10° C. to 60° C.

38. The method as claimed in claim 37 wherein the reduction is carried out at a temperature of about 40° C.

39. The method as claimed in claim 22 wherein the reaction is carried out in the dark.

40. The method as claimed in claim 22 wherein the reaction is carried out in ambient light conditions.

41. The method as claimed in claim 22 wherein the reaction is carried out under controlled irradiation conditions.

42. The sensor as claimed in claim 1 wherein the silver nanoparticles have an average size of 20 nm±8 nm.

43. The sensor as claimed in claim 1 wherein the silver nanoparticles have an average size of 22 nm±8 nm.

44. A sensor for biosensing comprising discrete silver nanoparticles that are stable and that are shaped and substantially plate-like in structure dispersed in an aqueous based system in which substantially all of the surfaces of the silver nanoparticles are available for interaction with an analyte or for functionalisation with a receptor which is capable of interacting with an analyte, wherein the silver nanoparticles provide a detectable change of from 1 to 150 nm in the position of their surface plasmon resonance in the UV-visible absorption spectrum in response to the binding of an analyte.

45. The sensor as claimed in claim 44 wherein the silver nanoparticles remain dispersed in the aqueous-based system.

46. The sensor as claimed in claim 44 wherein the silver nanoparticles remain dispersed in the aqueous-based system for a period of at least 8 months.

* * * * *